United States Patent
Shahrzad et al.

(10) Patent No.: US 11,527,308 B2
(45) Date of Patent: Dec. 13, 2022

(54) ENHANCED OPTIMIZATION WITH COMPOSITE OBJECTIVES AND NOVELTY-DIVERSITY SELECTION

(71) Applicant: Cognizant Technology Solutions U.S. Corporation, College Station, TX (US)

(72) Inventors: Hormoz Shahrzad, Dublin, CA (US); Daniel Edward Fink, Berkeley, CA (US); Risto Miikkulainen, Stanford, CA (US)

(73) Assignee: Cognizant Technology Solutions U.S. Corporation, College Station, TX (US)

( * ) Notice: Subject to any disclaimer, the term of this patent is extended or adjusted under 35 U.S.C. 154(b) by 983 days.

(21) Appl. No.: 16/268,463

(22) Filed: Feb. 5, 2019

(65) Prior Publication Data

US 2019/0244686 A1    Aug. 8, 2019

Related U.S. Application Data

(60) Provisional application No. 62/658,859, filed on Apr. 17, 2018, provisional application No. 62/627,125, filed on Feb. 6, 2018.

(51) Int. Cl.
| | |
|---|---|
| *G16H 10/20* | (2018.01) |
| *G06K 9/62* | (2022.01) |
| *G16H 50/70* | (2018.01) |
| *G16H 10/40* | (2018.01) |
| *G16H 50/20* | (2018.01) |

(52) U.S. Cl.
CPC ........... *G16H 10/20* (2018.01); *G06K 9/6231* (2013.01); *G06K 9/6257* (2013.01); *G16H 10/40* (2018.01); *G16H 50/20* (2018.01); *G16H 50/70* (2018.01)

(58) Field of Classification Search
CPC ........ G16H 10/20; G16H 10/40; G16H 50/70; G16H 50/20; G06K 9/6231; G06K 9/6257
See application file for complete search history.

(56) References Cited

U.S. PATENT DOCUMENTS

| | | | |
|---|---|---|---|
| 5,140,530 | A | 8/1992 | Guha et al. |
| 5,761,381 | A | 6/1998 | Arci et al. |
| 5,845,266 | A | 12/1998 | Lupien et al. |
| 5,920,848 | A | 7/1999 | Schutzer et al. |

(Continued)

FOREIGN PATENT DOCUMENTS

| | | |
|---|---|---|
| EP | 0762294 A2 | 3/1997 |
| EP | 2422276 | 2/2012 |

(Continued)

OTHER PUBLICATIONS

Baddar, Finding Better Sorting Networks (Year: 2009).*

(Continued)

*Primary Examiner* — Aryan E Weisenfeld
(74) *Attorney, Agent, or Firm* — Dawn-Marie Bey; Bey & Cotropia PLLC

(57) ABSTRACT

A composite novelty method approach to deceptive problems where a secondary objective is available to diversify the search is described. In such cases, composite objectives focus the search on the most useful tradeoffs and allow escaping deceptive areas. Novelty-based selection increases exploration in the focus area, leading to better solutions, faster and more consistently and it can be combined with other fitness-based methods.

16 Claims, 14 Drawing Sheets

(56) References Cited

U.S. PATENT DOCUMENTS

| | | | |
|---|---|---|---|
| 5,930,780 | A | 7/1999 | Hughes et al. |
| 6,240,399 | B1 | 5/2001 | Frank et al. |
| 6,249,783 | B1 | 6/2001 | Crone et al. |
| 7,013,344 | B2 | 3/2006 | Megiddo |
| 7,246,075 | B1 | 7/2007 | Testa |
| 7,370,013 | B1 | 5/2008 | Aziz et al. |
| 7,444,309 | B2 | 10/2008 | Branke et al. |
| 8,527,433 | B2 | 9/2013 | Hodjat et al. |
| 8,639,545 | B2 | 1/2014 | Cases et al. |
| 8,768,811 | B2 | 7/2014 | Hodjat et al. |
| 8,909,570 | B1 | 12/2014 | Hodjat et al. .................. 706/13 |
| 8,918,349 | B2 | 12/2014 | Hodjat et al. |
| 8,977,581 | B1 | 3/2015 | Hodjat et al. .................. 706/13 |
| 9,002,759 | B2 | 4/2015 | Hodjat et al. .......... G06N 3/126 |
| 9,053,431 | B1 | 6/2015 | Commons |
| 9,466,023 | B1 | 10/2016 | Shahrzad et al. ...... G06N 3/086 |
| 9,785,886 | B1 | 10/2017 | Andoni |
| 2002/0019844 | A1 | 2/2002 | Kurowski et al. |
| 2002/0080169 | A1 | 6/2002 | Diederiks |
| 2003/0014379 | A1 | 1/2003 | Saias et al. |
| 2003/0158887 | A1 | 8/2003 | Megiddo |
| 2004/0143559 | A1 | 7/2004 | Ayala |
| 2004/0210545 | A1 | 10/2004 | Branke et al. |
| 2004/0254901 | A1 | 12/2004 | Bonabeau et al. |
| 2005/0033672 | A1 | 2/2005 | Lasry et al. |
| 2005/0136480 | A1 | 6/2005 | Bralnnachuri et al. |
| 2005/0187848 | A1 | 8/2005 | Bonissone et al. |
| 2005/0197875 | A1 | 9/2005 | Kauffman |
| 2005/0198103 | A1 | 9/2005 | Ching |
| 2006/0218107 | A1 | 9/2006 | Young |
| 2007/0100907 | A1 | 5/2007 | Bayer |
| 2007/0143198 | A1 | 6/2007 | Brandes et al. |
| 2007/0143759 | A1 | 6/2007 | Ozgur et al. |
| 2007/0150435 | A1 | 6/2007 | Murakawa et al. |
| 2007/0185990 | A1 | 8/2007 | Ono et al. |
| 2008/0071588 | A1 | 3/2008 | Eder |
| 2008/0228644 | A1 | 9/2008 | Birkestrand et al. |
| 2009/0125370 | A1 | 5/2009 | Blondeau et al. |
| 2009/0307638 | A1 | 12/2009 | McConaghy |
| 2009/0327178 | A1 | 12/2009 | Jacobson |
| 2010/0030720 | A1 | 2/2010 | Stephens |
| 2010/0111991 | A1 | 5/2010 | Raitano et al. |
| 2010/0182935 | A1 | 7/2010 | David |
| 2010/0256795 | A1 | 10/2010 | McLaughlin et al. |
| 2010/0257228 | A1 | 10/2010 | Staggs et al. |
| 2010/0257605 | A1 | 10/2010 | McLaughlin et al. |
| 2010/0274736 | A1 | 10/2010 | Hodjat et al. |
| 2010/0274742 | A1 | 10/2010 | Hodjat et al. |
| 2010/0293119 | A1 | 11/2010 | Ferringer et al. |
| 2011/0161264 | A1 | 6/2011 | Cantin |
| 2011/0246834 | A1 | 10/2011 | Rajashekara et al. |
| 2012/0239517 | A1 | 9/2012 | Blondeau et al. |
| 2012/0239592 | A1 | 9/2012 | Esbensen |
| 2012/0313798 | A1 | 12/2012 | Markram |
| 2013/0124440 | A1 | 5/2013 | Hodjat et al. |
| 2013/0254142 | A1 | 9/2013 | Hodjat et al. |
| 2013/0311412 | A1 | 11/2013 | Lazar et al. |
| 2014/0006316 | A1 | 1/2014 | Hodjat et al. |
| 2014/0011982 | A1 | 1/2014 | Marasco et al. |
| 2015/0288573 | A1 | 10/2015 | Baughman et al. |
| 2016/0048753 | A1 | 2/2016 | Sussillo et al. |
| 2016/0063359 | A1 | 3/2016 | Szegedy et al. |
| 2016/0283563 | A1 | 9/2016 | Hodjat et al. |
| 2016/0329407 | A1 | 11/2016 | Takemura |
| 2016/0364522 | A1 | 12/2016 | Frey et al. |
| 2017/0060963 | A1 | 3/2017 | Whittaker et al. |
| 2017/0109355 | A1 | 4/2017 | Li et al. |
| 2017/0148433 | A1 | 5/2017 | Catanzaro et al. |
| 2017/0193367 | A1 | 7/2017 | Miikkulainen et al. |
| 2017/0213156 | A1 | 7/2017 | Hammond et al. |
| 2017/0256254 | A1 | 9/2017 | Huang |
| 2017/0323219 | A1 | 11/2017 | Shahrzad et al. .... G06N 99/005 |
| 2017/0323636 | A1 | 11/2017 | Xiao et al. |
| 2018/0053092 | A1 | 2/2018 | Hajizadeh |
| 2018/0114115 | A1 | 4/2018 | Liang et al. |
| 2018/0114116 | A1 | 4/2018 | Liang et al. |
| 2018/0240041 | A1 | 8/2018 | Koch et al. |
| 2018/0250554 | A1* | 9/2018 | Meyerson .......... A63B 24/0062 |
| 2019/0065954 | A1 | 2/2019 | Bittner, Jr. et al. |

FOREIGN PATENT DOCUMENTS

| | | |
|---|---|---|
| EP | 2422278 | 2/2012 |
| JP | 08-110804 | 4/1996 |
| JP | H09114797 | 5/1997 |
| JP | 2001325041 | 11/2001 |
| JP | 2003044665 | 2/2003 |
| JP | 2004240671 | 8/2004 |
| JP | 2004302741 | 10/2004 |
| JP | 2005190372 | 6/2007 |
| JP | 2007207173 | 8/2007 |
| JP | 2007522547 | 8/2007 |
| JP | 2008129984 | 6/2008 |
| WO | WO2017/161233 | 9/1917 |
| WO | WO2018/211138 | 11/1918 |
| WO | WO2018/213840 | 11/1918 |
| WO | WO 2005/073854 | 8/2005 |
| WO | WO 2010/120440 | 10/2010 |
| WO | WO 2010/127039 | 11/2010 |
| WO | WO 2010/127042 | 11/2010 |

OTHER PUBLICATIONS

Lehman, Joel, et al., "Exploiting open-endedness to solve problems through the search for novelty," Alife, 2008.

U.S. Appl. No. 13/184,307, filed Jul. 15, 2011 entitled "Data Mining Technique with Experience-Layered Gene Pool," 47 pages.

Hodjat, B., et al., "Introducing an Age-Varying Fitness Estimation Function," Genetic Finance, Chapter 5, Genetic Programming Theory and Practice, Springer Science+Business Media New York, Copyright 2013, pp. 59-71.

U.S. Appl. No. 14/595,991—Office Action dated May 10, 2017, 32 pages.

Hodjat et. al., "nPool: Massively Distributed Simultaneous Evolution and Cross-Validation in EC-Star," Sentient Technologies, May 2015, pp. 1-12.

Al-Haj Baddar, "Finding Better Sorting Networks," Dissertation to Kent State University for PhD, May 2009, 86 pages.

Cuccu, G., et al., "When Novelty is Not Enough," vol. 6624 in Lecture Notes in Computer Science, published in Applications of Evolutionary Computation, Springer-Verlag Berlin Heidelberg, Copyright 2011, pp. 234-243.

Gomes et al., "Devising Effective Novelty Search Algorithms: A Comprehensive Empirical Study," GECCO '15, Madrid, Spain, Jul. 11-15, 2015, ACM (Copyright 2015), 8 pages.

Gomes et al., "Evolution of Swarm Robotics Systems with Novelty Search," published in Swarm Intelligence, vol. 7, Issue 2, ANTS Special Issue, 2013, pp. 115-144.

Gomes et al., "Progressive Minimal Criteria Novelty Search," Lisboa, Portugal, cited in Advances in Artificial Intelligence, Springer-Verlag Berlin Heidelberg, Copyright 2012, pp. 281-290.

Gupta et al., "An Overview of methods maintaining Diversity in Generic Algorithms," International Journal of Emerging Technology and Advanced Engineering, vol. 2, Issue 5, May 2012, pp. 56-60.

Hodjat et al, "Maintenance of a Long Running Distributed Genetic Programming System for Solving Problems Requiring Big Data," Genetic Finance Chap 1, published in Genetic Programming Theory and Practice XI as Chapter 4, 2014, 20 pages.

Kipfer et al., "UberFlow: A GPU-Based Particle Engine," Computer Graphics and Visualization, the Eurographics Association, Copyright 2004, 9 pages.

Krcah et al., "Combination of Novelty Search and Fitness-Based Search Applied to Robot Body-Brain Co-Evolution," Charles University, Prague Czech Republic, in Proceedings of the 13th Czech-Japan Seminar on Data Analysis and Decision Making in Service Science, 2010, 6 pages.

(56) References Cited

OTHER PUBLICATIONS

Lehman et al., "Abandoning Objectives: Evolution through the Search for Novelty Alone," Evolutionary Computation journal, (19):2, MIT Press, Copyright 2011, pp. 189-223.
Lehman et al., "Efficiently Evolving Programs through the Search for Novelty," Proceedings of the Genetic and Evolutionary Computation Conference, ACM, New York NY, Copyright 2010, 8 pages.
Lehman et al., "Evolving a Diversity of Creatures through Novelty Search and Local Competition," Proceedings of the Genetic and Evolutionary Computation Conference, ACM, New York, NY, 2011, 8 pages.
Lehman et al., "Extinction Events Can Accelerate Evolution," PLOS One, journal.pone.0132886, Aug. 12, 2015, 16 pages.
Lehman et al., "Overcoming Deception in Evolution of Cognitive Behaviors," University of Texas at Austin, ACM, Jul. 12-16, 2014, 8 pages.
Lehman et al., "Revising the Evolutionary Computation Abstraction: Minimal Criteria Novelty Search," Proceedings of the Genetic and Evolutionary Computation Conference, GECCO 2010, ACM, 2010, 8 pages.
Mouret et al., "Encouraging Behavioral Diversity in Evolutionary Robotics: An Empirical Study," Massachusetts Institute of Technology, Copyright 2012, Evolutionary Computation 20(1), Spring, 2012, pp. 91-133.
Oreilly, U., et al., "EC-Star: A Massive-Scale, HUB and Spoke, Distributed Genetic Programming System," Evolutionary Design and Optimization Group, published in Genetic Programming Theory and Practice X as Chapter 6, published in V as Chap 1, Springer New York, Copyright 2013, 13 pages.
Salge, C., et al., "Empowerment—an Introduction," published in Guided Self-Organization: Inception, Chap 4, University of Hertfordshire, Copyright 2013, pp. 67-114.
Secretan, J., et al., "Picbreeder: A Case Study in Collaborative Evolutionary Exploration of Design Space," Evolutionary Computation journal, MIT Press, Copyright 2011, 30 pages.
Shahrzad, H., et al., "Tackling the Boolean Multiplexer Function Using a Highly Distributed Genetic Programming System," published in Genetic Programming Theory and Practice XII, Springer International Publishing, Copyright 2015, pp. 167-179.
Valsalam, V.K., et al., "Using Symmetry and Evolutionary Search to Minimize Sorting Networks," Journal of Machine Learning Research 14, the University of Texas at Austin, Department of Computer Science, 2013, pp. 303-331.
Wissner-Gross, et al., "Causal Entropic Forces," Physical Review Letters, PRL 110, 168702, American Physical Society, Apr. 19, 2013, 5 pages.
International Search Report and Written Opinion for PCT Application No. PCT/US18/66610, dated Apr. 15, 2019, 8 pp.
U.S. Appl. No. 14/595,991—Response to Office Action dated May 10, 2017, filed Nov. 10, 2017, 29 pages.
U.S. Appl. No. 14/595,991—Final Office Action dated Feb. 27, 2018, 25 pages.
U.S. Appl. No. 14/595,991—Response to Final Office Action dated Feb. 27, 2018, filed Jul. 27, 2018, 41 pages.
U.S. Appl. No. 14/595,991—Response to Final Office Action dated Feb. 27, 2018, filed May 22, 2018, 32 pages.
Stanley et al., Why greatness cannot be planned: the myth of the objective, Genet. Program Evolvable Mach.,m 16:559-561, 2015.
U.S. Appl. No. 13/943,630—Office Action dated May 27, 2015, 42 pages.
U.S. Appl. No. 13/945,630—Final Office Action dated Aug. 4, 2015, 22 pages.
U.S. Appl. No. 13/945,630—Resonse to Office Action dated Mar. 12, 2015 filed Jul. 13, 2015, 9 pages.
U.S. Appl. No. 13/358,381—Amendment After Allowance filed Feb. 13, 2015, 20 pages.
U.S. Appl. No. 13/943,630—Response to Office Action dated May 27, 2015 filed Sep. 23, 2015, 8 pages.
U.S. Appl. No. 14/539,908—Office Action dated Oct. 1, 2015, 33 pages.
U.S. Appl. No. 13/945,630—Response to Final Office Action dated Aug. 4, 2015 filed Nov. 4, 2015, 12 pages.
U.S. Appl. No. 13/945,630—Notice of Allowance dated Nov. 18, 2015, 8 pages.
U.S. Appl. No. 13/943,630—Notice of Allwoance dated Jan. 21, 2016, 28 pages.
U.S. Appl. No. 14/539,908—Response to Office Action dated Oct. 1, 2015 filed Feb. 1, 2016, 18 pages.
Hodjat et al., "Chapter 5: Introducing an Age-Varying Fitness Estimation Function." Genetic Programming Theory and Practice X. Ed. Riolo et al., Springer Apr. 19, 2013, pp. 59-71.
Caruana, R. Multitask learning. In Learning to learn, pp. 95-133. Springer US, 1998, (Year: 1998).
Rennie, Annealed dropout training of deep networks, 2014 IEEE Spoken Language Technology Workshop (SLT) 2014 (Year: 2014).
Loy C.C. Tang X. Zhang Z., Luo P. Facial landmark detection by deep multi-task learning. In Proceedings of ECCV'14, 2014 (Year: 2014).
Dong, D., Wu, H., He, W., Yu, D., and Wang, H. Multi-task learning for multiple language translation. In Proc. of ACL, pp. 1723-1732, 2015 (Year: 2015).
Li, Xiaodong, and Michael f{irley. 'The effects of varying population density in a fine-grained parallel genetic algcrithmi' Evolutionary Computation. 2002. CEC'02. Proceedings of the 2002 Congress on. vol. 2. IEEE. 2002.
Fidelis. Marcos Vinicius, Heitor S. Lopes, and Alex A. Freitas. "Discovering comprehensible classification rules with a genetic algorithm." Evolutionary Computation. 2000. Proceedings of the 2000 Congress on. vol. 1. IEEE. 2000.
Dec. 23, 2008 International Search Report and Written Opinion for PCT/US2008/82876, 10 pp.
Nov. 26, 2012 Extend EP SR for EP 08847214, 9 pp.
Jun. 16, 2011 Written Opinion from Singapore Patent Office in related application SG 201003127-6, 9 pp.
Apr. 20, 2012 Exam Report for related application AU 2008323758, 2 pp.
U.S. Appl. No. 14/014,063—Office Action dated May 7, 2014, 19 pages.
JP 2012-508663—Office Action dated Apr. 1, 2014, 6 pages (with English Translation).
JP 2012-508660—Office Action dated Apr. 1, 2014, 8 pages (with English Translation).
Supplementary European Search Report dated Oct. 12, 2012 in EP 10770288.
Supplementary European Search Report dated Oct. 9, 2012 in EP 10770287.
U.S. Appl. No. 13/895,238—Office Action dated Jan. 2, 2014, 17 pages.
Aug. 1, 2012 Office Action in U.S. Appl. No. 13/443,546, 12 pp.
Jun. 22, 2011 Office Action in U.S. Appl. No. 12/267,287, 16 pp.
Jul. 27, 2012 Final Office Action in U.S. Appl. No. 12/267,287, 14 pp.
AU 2010241594—Examination Report dated Oct. 8, 2013, 3 pages.
AU 2010241597—Examination Report dated Nov. 4, 2013, 4 pages.
U.S. Appl. No. 15/794,913—Non-Provisional Application filed Oct. 26, 2017, 73 pages.
Stanley, Kenneth O., et al., "Real-Time Evolution of Neural Networks in the Nero Video Game," AAAI, vol. 6, 2006, 4 pp.
Scott, E. O., et al., "Understanding Simple Asynchronous Evolutionary Algorithms," Jan. 17-20, 2015, 15 pp.
Kenneth O. Stanley and Risto Miikkulainen, "Evolving Neural Networks Through Augmenting Topologies," Evolutionary Computation, 10(2):99-127, 2002.
International Search Report and Written Opinion for PCT Application No. PCT/US18/64428, dated Mar. 26, 2019, 12 pp.
International Search Report and Written Opinion for Application No. PCT/US2018/064520, dated Mar. 4, 2019, 8 pp.
Xu, et al., "Inference of Genetic Regulatory Networks With Recurrent Neural Network Models Using Particle Swarm Optimization," Missouri University of Science and Technology, Oct. 2017 [retrieved

(56) References Cited

OTHER PUBLICATIONS on Feb. 14, 2019], Retrieved from the Internet: http://scholarsmine.mst.edu/cgi/viewcontent.cgi?article=1751&context=ele_comeng_facwork.
N. Garcia-Pedrajas, et al., "Cooperative Coevolution of Artificial Neural Nedtwork Ensembles for Pattern Classification," IEEE Transactions on Evolutionary Computation, vol. 9, No. 3, Jun. 2005, 32 pp.
Snoek, et al., "Scalable Bayesian Optimization Using Deep Neural Networks", 2015, 13 pages.
Fernando et al., "Pathnet: Evolution channels gradient descent in super neural networks," arXiv preprint arXiv:1701.08734 (2017), 16 pages.
Yang et al., "Deep multi-task representation learning: A tensor factorisation approach," arXiv preprint arXiv:1605.06391 (2016), 12 pages.
Shazeer et al., "Outrageously large neural networks: The sparsely-gated mixture-of-experts layer," arXiv preprint arXiv:1701.06538 (2017), 19 pages.
Misra et al., "Cross-stitch networks for multi-task learning," In Proceedings of the IEEE Conference on Computer Vision and Pattern Recognition, pp. 3994-4003, 2016.
James Bradbury, et al., "Quasi-Recurrent Neural Networks," arXiv:1611.01576v2, Nov. 21, 2016, 11 pp.; Retrieved from the Internet: https//arxiv.org/pdf/1611.01576.pdf?fbclid=1wAR3hreOvBGmJZe54-631X49XedcbsQoDYIRu87BcCHEBf_vMKF8FDKK_7Nw.
Yin, et al., "ABCNN: Attention-Based Convolutional Neural Network for Modeling Sentence Pairs," Transactions of the Association for Computational Linguistics, vol. 4, pp. 259-272, 2016, Retrieved on Aug. 4, 2019, Retrieved from the Internet: https://www.mitpressjounrals.org/doi/pdf/10.1162/tacl_a_00097.
International Search Report and Written Opinion for PCT Application No. PCT/US2019/017175, dated Jun. 5, 2019, 10 pp.
E. Meyerson and R. Miikulainen, "Pseudo-Task Augmentation: From Deep Multitask Learning to Intratask Sharing and Back," ICML, 2018.
J. Z. Liang, et al., "Evolutionary Architecture Search for Deep Multitask Networks," GECCO, 2018.
E. Meyerson and R. Miikkulainen, "Beyond Shared Hierarchies: Deep Multitask Learning Through Soft Layer Ordering," ICLR, 2018.
R. Miikkulainen, et al., "Evolving Deep Neural Networks," arXiv prepring arXiv:1703.00548, 2017.
Bilen, et al., "Integrated Perception with Recurrent Multi-Task Neural Networks," NIPS, 2016, 9 pp.
International Search Report and Written Opinion for PCT App. No. PCT/US19/61198, dated Mar. 11, 2020, 15 pp.
Moriarty, David E., et al., "Forming neural networks through efficient and adaptive coevolution," Evolutionary Computation 5.4, 1997.
Lee, Chi-Ho, et al., "Evolutionary ordered neural network with a linked-list encoding scheme," Proceedings of IEEE International Conference on Evolutionary Computation, IEEE, 1996.
Bredeche, Nicolas, et al., "On-line, on-board evolution of robot controllers," International Conference on Artificial Evolution, Springer, Berlin, Heidelberg, 2009.
Utech, J., et al., "An evolutionary algorithm for drawing directed graphs," Proc. of the Int. Conf. on Imaging Science, Systems and Technology, 1998.
International Preliminary Report on Patentability for PCT App. PCT/US2019/061198, dated Nov. 18, 2020, 24 pp.
Pantridge, et al., "Evolution of Layer Based Neural Networks: Preliminary Report," GECCO '16, pp. 1015-1022, Jul. 2016.
International Search Report and Written Opinion for PCT Application No. PCT/US18/65472, dated Mar. 27, 2019, 8 pp.
U.S. Appl. No. 15/794,913 titled "Cooperative Evolution of Deep Neural Network Structures," filed Oct. 26, 2017.
U.S. Appl. No. 15/915,028, titled "Asynchronous Evaluation Strategy for Evolution of Deep Neural Networks," filed Mar. 3, 2018.
Risto Miikkulainen, "Evolving Multitask Neural Network Structure," The University of Texas at Austin and Sentient Technologies, Inc., Aug. 26, 2013.
Rosenbaum, et al., "Routing Networks: Adaptive Selection of Non-Linear Funcdtions For Multi-Task Learning," In: Cornell University Library/Computer Science/Machine Learning, Dec. 31, 2017 [online] [retrieved on Mar. 15, 2019], Retrieved from the Internet: https://arxiv.org/abs/1711.01239v2.
Bonadiman et al., "Multitask Learning with Deep Neural Networks for Community Question Answering," In: Cornell University Library/Completer Science/Machine Learning, Feb. 13, 2017 [online] [retrieved on Mar. 15, 2019], Retrieved from the Internet: https://arxiv.org/abs/1702.03706.
Ruder, "An Overview of Multi-Task Learning in Deep Neural Networks," In: Cornell University Library/Computer Science/Machine Learning, Jun. 15, 2017 [online] [retrieved on Mar. 15, 2019], Retrieved from the Internet: https://arxiv.org/abs/1706.05098.
Hodjat et el., "Chapter 5: Introducing an Age-Varying Fitness Estimation Function." Genetic Programming Theory and Practice X. Ed. Riolo et al., Springer Apr. 19, 2013, pp. 59-71.
Gonzalez, et al., "Evolving Loss Functions With Multivariate Taylor Polynomial Parameterizations," Version 1, published arXiv: 2002.00059v1, Jan. 31, 2020.
Gonzalez, et al., "Evolving Loss Functions With Multivariate Taylor Polynomial Parameterization," Version 2, published arXiv: 2002.00059v2), Feb. 10, 2020.
Gonzalez, et al., "Optimizing Loss Functions Through Multivariate Taylor Polynomial Parameterization," Version 3 (published arXiv:2002.00059v3), Jun. 6, 2020.
N. Hansen, et al, "Adapting arbitrary normal mutation distributions in evolution strategies: The covariance matrix adaptation," In Proceedings of IEEE International Conference on Evolutionary Computation, pp. 312-317, IEEE, 1996.
Hansen, et al., "Completely derandomized self-adaptation in evolution strategies," Evolutionary Computation, vol. 9, No. 2, pp. 159-195, 2001.
N. Hansen, et al., "Evaluating the CMA evolution strategy on multimodal test functions," International Conference on Parallel Problem Solving from Nature, Springer, pp. 282-291, 2004.
H. Li, et al., "Visualizing the loss landscape of neural nets," Advances in Neural Information Processing Systems 31, pp. 6389-6399 (Curran Associates, Inc., 2018), arXiv:1712.09913v3, Nov. 7, 2018.
Liang, et al, "Population-Based Training for Loss Function Optimization," arXiv:2002.04225v1 (Feb. 11, 2020).
"Python vs. R for Artificial Intelligence, Machine Learning, and Data Science," by Scenario or Task by Alex Castrounis of Innoarchitech, published online by O'Reilly Media, Copyright InnoArchiTech LLC 2020 [retrieved on Oct. 16, 2020], Retrieved from the Internet: https://www.innoarchitech.com/blog/python-vs-or-r-artificial-intelligence-ai-machine-learning-data-science-which-use, 27 pp.
Production vs Development Artificial Intelligence and Machine Learning, by Alex Castrounis of Innoarchitech, published online by O'Reilly Media, Copyright InnoArchiTech LLC 2020 [retrieved on Oct. 16, 2020], Retrieved from the Internet: https://www.innoarchitech.com/blog/development-vs-or-production-batch-offline-online-automated-artificial-intelligence-ai-machine-learning, 24 pp.
"Advanced Analytics Packages, Frameworks, and Platforms," by Alex Castrounis of Innoarchitech, published online by O'Reilly Media, Copyright InnoArchiTech LLC 2020 [retrieved Oct. 16, 2020], Retrieved from the Internet: https://www.innoarchitech.com/blog/packages-frameworks-platforms-by-scenario-task-artificial-intelligence-ai-machine-learning-data-science, 29 pp.
Santiago Gonzalez, "Loss Function Optimization Using Evolutionary Computation and Multivariate Function Approximators, Particularly Multivariate Taylor Expansions," 5 pp., Aug. 22, 2019.
Santiago Gonzalez, et al., "Improved Training Speed, Accuracy, and Data Utilization Through Loss Function Optimization," Version 1, arXiv: 1905.11528v1, dated May 27, 2019.
Santiago Gonzalez, et al., "Improved Training Speed, Accuracy, and Data Utilization Through Loss Function Optimization," Version 2, arXiv: 1905.11528v2, dated Feb. 10, 2020.

(56) References Cited

OTHER PUBLICATIONS

Santiago Gonzalez, et al., "Improved Training Speed, Accuracy, and Data Utilization Through Loss Function Optimization," Version 3, arXiv: 1905.11528v3, dated Apr. 27, 2020.
J. T. Barron, "A General and Adaptive Robust Loss Function," arXiv: 1701.03077v6, 2018.
K. Janocha and W. M. Czarnecki, "On Loss Functions for Deep Neural Networks in Classification," arXiv: 1702.05659, 2017.
A. Krizhevsky, et al., "ImageNet Classification With Deep Convolutional Neural Networks," NIPS'12: Proceedings of the 25th International Conference on Neural Information Processing Systems, vol. 1, Dec. 2012, pp. 1097-1105.
"CS 224D: Deep Learning for NLP, Lecture Note: Part III", 14 pp., Spring, 2016.
"CS 224D: Deep Learning for NLP, Lecture Notes: Part IV", 12 pp., Spring, 2015.
"CS 224D: Deep Learning for NLP, Lecture Notes: Part V", 6 pp., Spring, 2015.
U.S. Appl. No. 62/468,224, titled "Asynchronous Evaluation Strategy for Evolution of Deep Neural Networks," filed Mar. 7, 2017.
Aditya Rawal and Risto Miikkulainen, "From Nodes to Networks: Evolving Recurrent Neural Networks," GECCO '18, Jul. 15-19, 2018, Kyoto, Japan.
Julian G. Zilly, Rupesh Kumar Srivastava, Jan Koutnik, and Jurgen Schmidhube, "Recurrent Highway Networks," CoRR abs/1607.03474, 2016 (Arxiv: 1607.03474).
U.S. Appl. No. 62/627,658, titled "From Nodes to Networks: Evolving Recurrent Neural Networks," filed Feb. 7, 2018.
U.S. Appl. No. 62/627,161, titled "From Nodes to Networks: Evolving Recurrent Neural Networks," filed Feb. 6, 2018.
U.S. Appl. No. 62/598,409, titled "Evolving Multitask Neural Network Structure," filed Dec. 13, 2017.
U.S. Appl. No. 13/540,507—Notice of Allowance and Fee(s) Due, dated Oct. 31, 2014, 9 pages.
U.S. Appl. No. 13/540,507—Response filed Oct. 15, 2014, 20 pages.
U.S. Appl. No. 13/358,381—Notice of Allowance and Fee(s) Due, dated Nov. 19, 2014, 5 pages.
U.S. Appl. No. 13/358,381—Response dated Oct. 3, 2014, 21 pages.
U.S. Appl. No. 13/184,307—Response dated Jun. 23, 2014, 32 pages.
U.S. Appl. No. 13/184,307—Response dated Jan. 22, 2014, 19 pages.
Hornby, G.S., "ALPS: The Age-Layered Population Structure for Reducing the Problem of Premature Convergence," GECCO'06, Seattle, Jul. 2006, authored by an employee of the US Government, therefore in the public domain, 8pp.
Hornby, G.S., "A Steady-Slate Version of the Age-Layered Population Structure EA," Chapter 1 of Genetic Programming Theory and Practice VII, Riolo et al., editors, Springer 2009, 16pp.
Hornby, G.S., "Steady-State ALPS for Real-Valued Problems," GECCO'09, Montreal, Jul. 2009, Assoc. for Computing Machinery, 8pp.
Idesign lab, "ALPS—the Age-Layered Population Structure," UC Santa Cruz web article printed Mar. 17, 2011, 3 pp. (http://idesign.ucsc.edu/projects/alps.html).
Laumanns, Marco et al.; "A Unified Model for Multi-Objectve Evolutionary Algorithms with Elitism"; 2000; IEEE; pp. 46-53.
Ahn, Chang Wook et al.; "Elitism-Based Compact Genetic Algorithms"; 2003; IEEE; Transactions on Evolutionary Computation, vol. 7, No. 4; pp. 367-385.
Gaspar-Cunha, A. et al., "A Multi-Objective Evolutionary Algorithm Using Neural Networks to Approximate Fitness Evaluations," Int'l J. Computers, Systems and Signals, 6(1) 2005, pp. 18-36.
Kosorukoff, A. "Using incremental evaluation and adaptive choice of operators in a genetic algorithm," Proc. Genetic and Evolutionary Computation Conference, GECCO—Sep. 2002, 7pp.
Nelson, A. "Fitness functions in evolutionary robotics: A survey and analysis," Robotics and Autonomous Systems 57 (Apr. 30, 2009) 345-370.
Bongard, J. C. et al., "Guarding Against Premature Convergence while Accelerating Evolutionary Search", GECCO'10: Proceedings of the 12th annual conference on Genetic and Evolutionary Computation, 8 pages (2010).
Wu, A.S. et al., "An incremental fitness function for partitioning parallel taks," Proc. Genetic and Evolutionary Computation Conf. (Aug. 2001) 8pp.
Whitehead, B.A. "Genetic Evolution of Radial Basis Function Coverage Using Orthogonal Niches," IEEE Transactions on Neural Networks, 7:6, (Nov. 1996) 1525-28.
Bui, L.T. et al., "Local models: An approach to distributed multi-objective optimization," Computational Optimization and Applications, vol. 42, No. 1, Oct. 2007, pp. 105-139.
Castillo, Tapia, et al., "Applications of multi-objective evolutionary algorithms in economics and finance: A survey," Proc. IEEE Congress on Evolutionary Computation, Sep. 2007, pp. 532-539.
Ducheyne, E. et al., "Is Fitness Inheritance Useful for Real-World Applications?" Evolutionary Multi-Criterion Optimization, ser. LNCS 2631, Spring 2003, pp. 31-42.
Enee, Gilles et al., "Classifier Systems Evolving Multi-Agent System with Distributed Elitism," Proc. 1999 Congress on Evolutionary Computation (CEC'99) vol. 3:6, Jul. 1999, pp. 1740-1746.
Gopalakrishnan, G. et al., "Optimal Sampling in a Noisy Genetic Algorithm for Risk-Based Remediation Design," Bridging the gap: meeting the world's water and environmental resources challenges, Proc. World Water Congress 2001, 8 pp.
Juille, H. "Evolution of Non-Deterministic Incremental Algorithms as a New Approach for Search in State Spaces," Proc. 6th Int'l Conf. on Genetic Algorithms, 1995, 8pp.
International Search Report dated Jul. 2, 2010 in PCT/US10/32847.
International Search Report dated Jun. 29, 2010 in PCT/US10/32841.
Sacks, J. et al. "Design and Analysis of Computer Experiments," Statistical Science 4:4, 1989, 409-435.
Torresen, J. "A Dynamic Fitness Function Applied to Improve the Generalisation when Evolving a Signal Processing Hardware Architecture," Proc. EvoWorkshops 2002, 267-299 (12 pp).
Bartlett II, J.E. et al., "Organizational Research: Determining Appropriate Sample Size in Survey Research," IT, Learning, and Performance Journal 19(1) Spring 2001, 8pp.
Fitzpatrick, J.M. et al., "Genetic Algorithms in Noisy Environments," Machine Learning 3: 101-120, May 1988.
JP 2010-533295, Office Action dated Apr. 16, 2013, 3 pages.
León C. et al., "Parallel hypervolume-quided hyperheuristic for adapting the multi-objective evolutionary island model," Proc. 3rd Int'l Workshop on Nature Inspired Cooperative Strategies for Optimization Studies in Computational Intelligence, vol. 236, Nov. 2008, pp. 261-272.
López Jaimes A. et al., "MRMOGA: Parallel evolutionary multiobjective optimization using multiple resolutions," Proc. IEEE Congress on Evolutionary Computation, vol. 3, Sep. 2005, pp. 2294-2301.
Davarynejad, M. et al., "A Novel General Framework for Evolutionary Optimization: Adaptive Fuzzy Fitness Granulation," CEC Sep. 2007, 6pp.
Davarynejad, M. "Fuzzy Fitness Granulation in Evolutionary Algorithms for complex optimization," Master of Science Thesis, Ferdowsi Univ. of Mashhad, Jun. 2007, 30pp.
Salami, M. et al., "A fast evaluation strategy for evolutionary algorithms," Applied Soft Computing 2/3F (Jan. 2003) 156-173.
Akbarzadeh-T., M-R, et al., "Friendship Modeling for Cooperative Co-Evolutionary Fuzzy Systems: A Hybrid GA-GP Algorithm," Proc. 22nd Int'l Conf. of N. American FIPS, Jul. 2003, pp. 61-66.
Mouret, J.B. et al., "Encouraging Behavioral Diversity in Evolutionary Robotics: An Empirical Study," MIT, Evolutionary Computation 20(1):91-133, 2012.
Myers, Raymond H. and Montgomery, Douglas C., Response Surface Methodology: Process and Product Optimization Using Designed Experiments, John Wiley and Sons, Inc., New York, 1995, 12 pages.
Poli, R., et al., "Genetic Programming: An Introductory Tutorial and a Survey of Techniques and Applications," Univ. Essex School of Computer Science and Electronic Engineering Technical Report No. CES-475, Oct. 2007, pp. 1-112.

(56) References Cited

OTHER PUBLICATIONS

Georgilakis, P.S. "Genetic Algorithm Model for Profit Maximization of Generating Companies in Deregulated Electricity Markets", Applied Artificial Intelligence, Jul. 2009, 23:6,538-552.

Refaeilzadeh, P. et al., "Cross Validation" entry, Encyclopedia of Database Systems, eds. Özsu and Liu, Springer, 2009, 6pp.

Remce, S. et al. "Evolution of Fitness Functions to Improve Heuristic Performance," LION Dec. 8-10, 2007 II. LNCS 5313 pp. 206-219.

Sakauchi et al., UNIFINE: A Next Generation Financial Solution System of Nihon Unisys Ltd., Technology Review 'UNISYS,' Japan, Nihon Unisys Ltd., Feb. 28, 2006, vol. 25, No. 4, 5 pages.

Schoreels C., "Agent based Genetic Algorithm Employing Financial Technical Analysis for Making Trading Decisions Using Historical Equity Market Data," IEEE/WIC/ACM International Conference on Intelligent Agent Technology (IAT2004), Beijing, China, Sep. 20-24, 2004, pp. 421-424.

Streichert F., "Introduction to Evolutionary Algorithms," paper to be presented Apr. 4, 2002 at the Frankfurt MathFinance Workshop Mar. 30, 2002, Frankfurt, Germany, XP55038571, 22 pp. (retrieved from the Internet: URL: http://www.ra.cs.uni-tuebingen.de/mita rb/streiche/publications/Introduction to E volutionary Algorithms.pdf).

Tanev, I. et al., "Scalable architecture for parallel distributed implementation of genetic programming on network of workstations," J. Systems Architecture, vol. 47, Jul. 2001, pp. 557-572.

U.S. Appl. No. 13/184,307—Office Action dated Oct. 21, 2013, 16 pages.

Hornby, Gregory S.,"The Age-Layered Population Structure (ALPS) Evolutionary Algorithm," ACM; GECCO Jul. 8-12, 2009; 7 pages.

U.S. Appl. No. 13/358,381—Office Action dated Jul. 8, 2014, 18 pages.

Freitas, A., "A review of evolutionary algorithms for data mining." Soft Computing for Knowledge Discovery and Data Mining, Springer US, 2008, pp. 79-111.

U.S. Appl. No. 13/540,507—Office Action dated Sep. 9, 2014, 25 pages.

U.S. Appl. No. 13/184,307—Notice of Allowance dated Aug. 4, 2014, 9 pages.

U.S. Appl. No. 13/184,307—Office Action dated Mar. 21, 2014, 36 pages.

U.S. Appl. No. 13/945,630—Office Action dated Mar. 12, 2015, 18 pages.

Koza, J. R., "Genetic Programming: On the Programming of Computers By Means of Natural Selection," MIT Press (1992).

Deb, et al., "A Fast and Elitist Multiobjective Genetic Algorithm: NSGA II," IEEE Transactions on Evolutionary Computation, vol. 6, No. 2 pp. 182-197, Apr. 2002.

\* cited by examiner

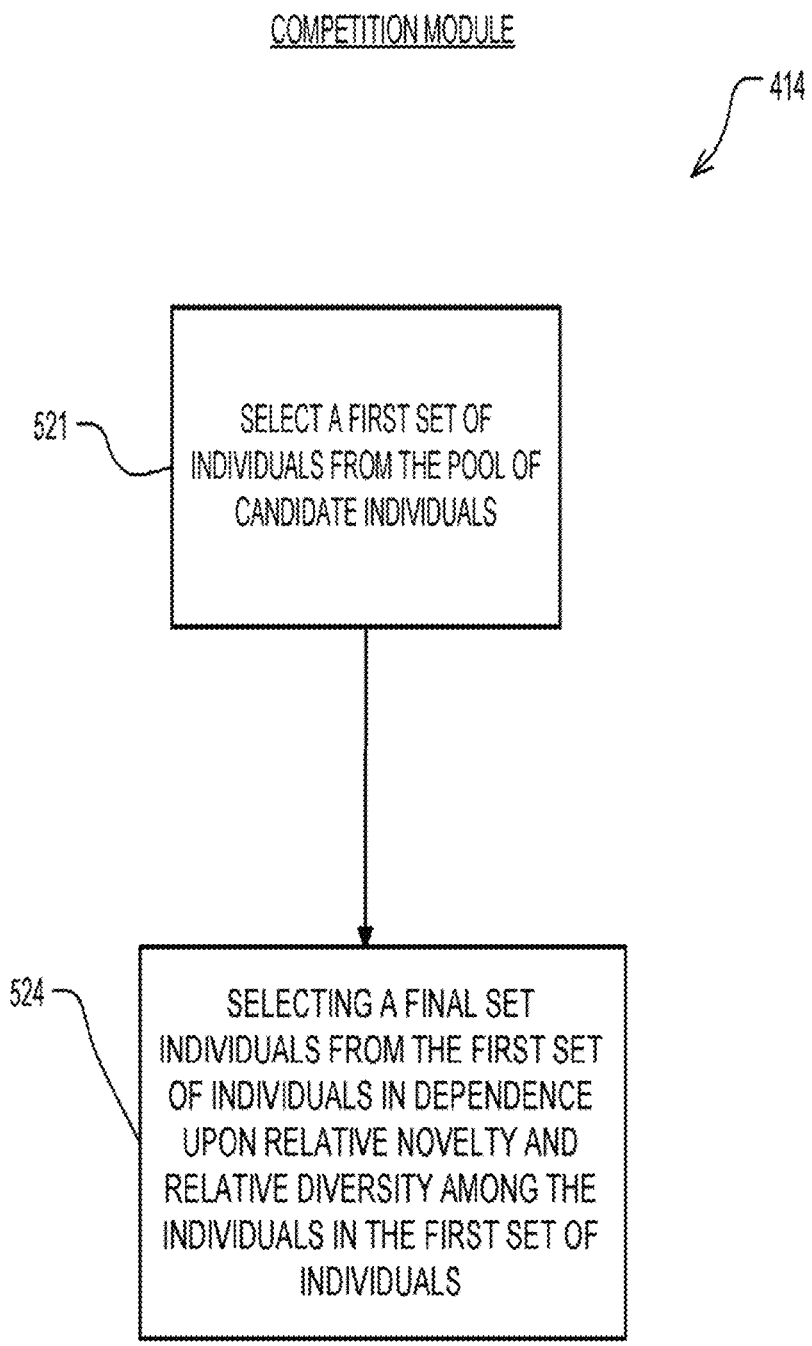

ENHANCED OPTIMIZATION WITH COMPOSITE OBJECTIVES AND NOVELTY-DIVERSITY SELECTION

CROSS-REFERENCE TO OTHER APPLICATIONS

This application claims the benefit of priority to U.S. Provisional Patent Application Nos. 62/627,125 and 62/658,859, similarly entitled "ENHANCED OPTIMIZATION WITH COMPOSITE OBJECTIVES AND NOVELTY SELECTION," filed on Feb. 6, 2018 and Apr. 17, 2018, both of which are incorporated herein by reference in their entireties.

This application cross-references the following patent applications and publications which are incorporated herein by reference in their entireties: U.S. Patent Publication No. 2017/0323219, published Nov. 9, 2017 entitled Data Mining Technique with Distributed Novelty Search; U.S. Pat. No. 8,909,570 entitled Data Mining Technique With Experience-layered Gene Pool; U.S. Pat. No. 8,977,581 entitled Data Mining Technique With Diversity Promotion; and U.S. Pat. No. 9,002,759 entitled Data Mining Technique With Maintenance Of Fitness History.

FIELD OF THE TECHNOLOGY DISCLOSED

The technology disclosed relates generally to a computer system that performs evolutionary algorithms better. More particularly, the computer system uses a multi-objective driven algorithm that is better able to find optimum solutions to a problem because it balances the use of objectives, composite functions, and relative novelty and diversity in evolutionary optimization.

BACKGROUND

In many environments, a large amount of data can be or has been collected which records experience over time within the environment. For example, a healthcare environment may record clinical data, diagnoses and treatment regimens for a large number of patients, as well as outcomes. A business environment may record customer information such as who they are and what they do, and their browsing and purchasing histories. A computer security environment may record a large number of software code examples that have been found to be malicious. Despite the large quantities of such data, or perhaps because of it, deriving useful knowledge from such data stores can be a daunting task.

The process of extracting patterns from such data sets is known as data mining. Many techniques have been applied to the problem, but the present discussion concerns a class of techniques known as genetic algorithms. Genetic algorithms have been applied to all of the above-mentioned environments.

Evolutionary algorithms, which are supersets of Genetic Algorithms, are good at traversing chaotic search spaces. According to Koza, J. R., "Genetic Programming: On the Programming of Computers by Means of Natural Selection," MIT Press (1992), incorporated by reference herein, an evolutionary algorithm can be used to evolve complete programs in declarative notation. The basic elements of an evolutionary algorithm are an environment, a model for a genotype (referred to herein as an "individual"), a fitness function, and a procreation function. An environment may be a model of any problem statement. An individual may be defined by a set of rules governing its behavior within the environment. A rule may be a list of conditions followed by an action to be performed in the environment. A fitness function may be defined by the degree to which an evolving rule set is successfully negotiating the environment. A fitness function is thus used for evaluating the fitness of each individual in the environment. A procreation function generates new individuals by mixing rules among the fittest parent individuals. In each generation, a new population of individuals is created.

A common difficulty of evolutionary algorithms is that they are increasingly faced with environments with multiple problem statements resulting in more than one search objective. For example, in a healthcare embodiment, an individual may have the objective of diagnosing an ailment accurately, and also the objective of a fast diagnosis. To support a multi-objective search, the data mining system may define a number of objectives so as to allow the evolution process to consider more than one objective. For example, in the healthcare embodiment described above with two objectives, the evolution process would search for individuals (solutions) that optimize each of the objectives. A large number of other objectives can be included depending on the target application. In the health care embodiment above, additional objectives, such as consistency, might be included in the multi-objective search space.

The presence of multiple objectives in a data mining environment, in principle, gives rise to a set of optimal solutions instead of a single optimal solution. Such optimal solutions are also known as Pareto-optimal solutions. In the absence of any further information, one of these Pareto-optimal solutions cannot be said to be better than the other.

One way to deal with the problem of multiple objectives is to define a composite function which is a linear combination of all the objectives, weighting each objective according to its perceived importance relative to the other objectives. This technique can work sometimes, but it does not take advantage of the fact that in many environments the objectives are not zero-sum alternatives: it may be possible to find solutions that optimize all objectives in light of each other, even though some objectives may not be satisfied to the same extent as they would if optimized individually.

Single-objective evolutionary algorithms suggest converting the multi-objective optimization problem to a single-objective optimization problem by emphasizing one particular Pareto-optimal solution at a time. When such a method is to be used for finding multiple solutions, it has to be applied many times, hopefully finding a different solution at each simulation run.

Multi-objective evolutionary algorithms can be used to find solutions in environments with multiple problem statements and more than one search objectives. A multi-objective evolutionary algorithm is able to find multiple Pareto-optimal solutions in one single simulation run. One such multi-objective evolutionary algorithm is the non-dominated sorting genetic algorithm (NSGA), described in more detail in an article by Deb, et al., titled "A Fast and Elitist Multiobjective Genetic Algorithm: NSGA II," IEEE Transactions on Evolutionary Computation, Vol. 6, No. 2, pp. 182-197, April, 2002, incorporated herein by reference.

While multi-objective evolutionary algorithms produce a diverse set of solutions, such diversity may not always be useful. Therefore, a multi-objective driven search is desired that focuses the search in more useful areas of the multi-objective search space. It is in this kind of environment that embodiments of the present invention reside. Focusing the search in more useful areas may result in loss of diversity. In order to prevent loss of diversity, relative novelty measure and diversity measure are taken into account during the selection of optimal individuals in the useful areas of the multi-objective search space. Therefore, the resulting evolutionary algorithm, i.e., composite novelty method, produces a diverse group of individuals in selected areas of a multi-objective search space.

SUMMARY

Roughly described, a computer system uses a multi-objective driven algorithm for optimizing a plurality of objectives in a focused area of a multi-objective search space without loss in diversity. The focused area in the multi-objective search space is defined by a plurality of composite functions. Each composite function is dependent on at least one of the objectives, and at least one of the composite functions is dependent on more than one of the objectives.

A computer-implemented evolutionary data mining system includes a memory storing a pool of candidate individuals. The data mining system further includes a processing unit which tests individuals from the candidate individual pool on training data and develops a respective objective value estimating the individual's level of success with respect to each of the objectives. A competition module of the data mining system utilizes a dominance filter to select a first set of individuals in the focused area of search. The dominance filter is dependent upon a plurality of composite values each calculated from a respective one of a plurality of composite functions. The data mining system selects a final set of individuals from the first set of individuals in dependence upon relative novelty and relative diversity among the individuals in the first set of individuals. A procreation module uses the final set of individuals for procreating new individuals and adding them to the pool of candidate individuals.

The competition module of the data mining system selects individuals from the pool of candidate individuals that are not dominated by any other individuals in the pool to form a first set of individuals. In order to determine whether an individual is dominated by other individuals in the pool of candidate individuals, the module evaluates the individual's dominance of said over every other individual in the pool. Though different embodiments can define dominance differently, in one embodiment a first individual in the pool is considered to dominate over a second individual in the pool if the composite value of the first individual is greater than composite value of the second individual for at least one corresponding composite function, and the composite value of the first individual is not lower than composite value of the second individual for any one of the corresponding composite functions.

During selection of a final set of individuals from the first set of individuals, the competition module of the data mining system determines an average novelty score for each individual in the first set of individuals, selects a predetermined number of individuals having greater novelty than all other individuals in the first set of individuals as indicated by their respective average novelty scores to form a second set of individuals, and forms a third set of individuals with individuals from the first set of individuals which are not selected for the second set of individuals. The competition module of the data mining system then substitutes individuals from the third set of individuals into the second set of individuals in a manner that improves the behavioral diversity of the individuals in the second set of individuals, to form the final set of individuals. In an embodiment, the competition module achieves this by, until the number of individuals in the third set of individuals reaches zero, adding an individual from the third set of individuals to the second set of individuals, selecting a pair of individuals from the enlarged second set of individuals that are least behaviorally diverse from each other, and discarding one individual from the pair using a predetermined filter.

The above summary of the invention is provided in order to provide a basic understanding of some aspects of the invention. This summary is not intended to identify key or critical elements of the invention or to delineate the scope of the invention. Its sole purpose is to present some concepts of the invention in a simplified form as a prelude to the more detailed description that is presented later. Particular aspects of the invention are described in the claims, specification, and drawings.

BRIEF DESCRIPTION OF THE DRAWINGS

The invention will be described with respect to specific embodiments thereof, and reference will be made to the drawings, in which:

FIGS. 5A, 5B and 5C illustrate a method of operation of the competition module in FIG. 4, according to an embodiment of the invention.

DETAILED DESCRIPTION

Figure 1:
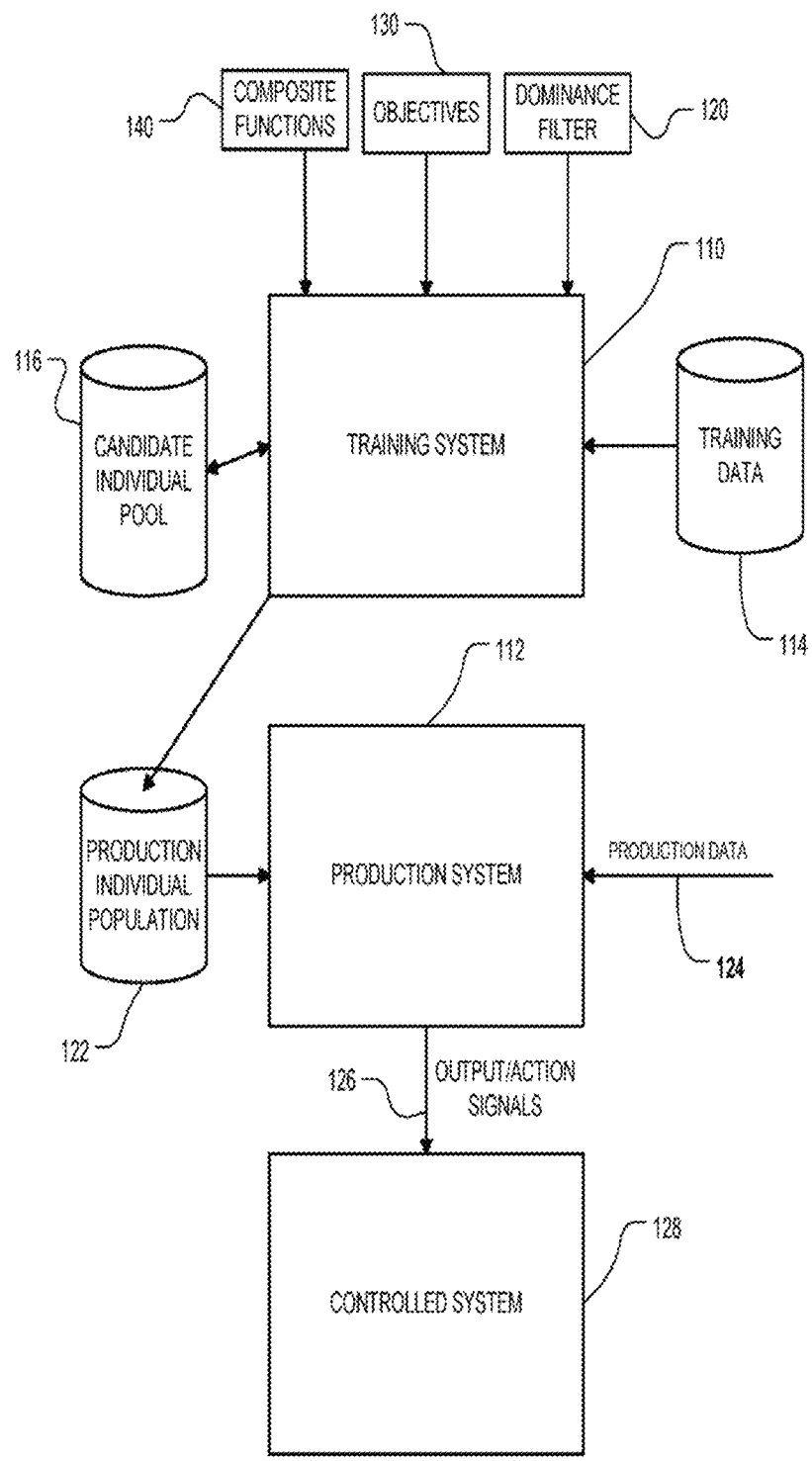
FIG. 1 is an overall diagram of an embodiment of a data mining system incorporating features of the invention.

The following description is presented to enable any person skilled in the art to make and use the invention and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

A multi-objective optimization problem can be defined as the problem of finding a set of solutions in a search space with a plurality of competing objectives. With multiple competing objectives, the aim is to find a set of solutions that are good compromises or "trade-offs" rather than a single solution as in a global optimization. One example of a multi-objective optimization problem with competing objectives is scheduling of truck routes by a transportation company. The competing objectives in the scheduling problem might include minimizing the number of miles driven by empty trucks, equalize workloads among truck drivers, follow Department of Transportation restrictions, etc. In real-world multi-objective optimization problems, there are trade-offs between the competing objectives. In other words, if a solution maximizes one objective, it is often at the expense of other objectives in the multi-objective search space.

The use of evolutionary algorithms to address the multi-objective optimization problem has been motivated by the population-based nature of evolutionary algorithms which allows the generation of a set of "trade-off" solutions or individuals. The set of "trade-off" solutions or individuals may be "Pareto optimal." As used herein, a solution or an individual is said to be "Pareto optimal" if the individual cannot improve the objective values of some objectives without causing a simultaneous degradation in the objective value of at least one other objective. A Pareto optimal individual cannot simultaneously improve the objective values of all the objectives in the multi-objective search space.

As used herein, the term "objective value" is a value estimating an individual's level of success with respect to one of the objectives in the multi-objective optimization problem. In some embodiments a higher objective value is better than a lower one, whereas in other embodiments a lower objective value is better than a higher one. In the description herein, a higher objective value is assumed to be better, and it will be understood that exactly the same concepts apply in embodiments in which a lower objective value is better. Also as used herein, exactness is considered to be a special case of estimation. For example, an objective value that reflects a level of success exactly, is also considered herein to be an "estimate" of such level of success.

Pareto optimization can have the effect of improving diversity among candidates, because they evolve and retain a range of solutions making different tradeoffs in objective space. However, not all such diversity is useful. For example, candidates that optimize one objective only and ignore the others are less likely to lead to useful tradeoffs, and are less likely to escape a deceptive landscape. In some embodiments herein, therefore, the system addresses this problem by replacing the objectives in the multi-objective search with certain composite functions of the objective (typically linear combinations of the objectives). This has the effect of focusing the search in more useful areas of the search space. In effect, the Pareto axes in objective space become angled, and search focuses more on tradeoffs instead of single objectives, allowing it to search around deceptive areas.

As used herein, a "composite function" is a function that is dependent on at least one of the objectives in the multi-objective optimization problem. At least two composite functions are used, and at least one of them is dependent on more than one of the objectives. For a multi-objective optimization problem with objectives a, b and c, an example plurality of composites functions may be defined as:

$$\text{Composite function } 1(a,b,c) = \alpha_1 a + \alpha_2 b + \alpha_3 c \quad (1)$$

$$\text{Composite function } 2(a,b,c) = \alpha_4 a + \alpha_5 b \quad (2)$$

$$\text{Composite function } 3(a,b,c) = \alpha_6 a + \alpha_7 c \quad (3)$$

where $\alpha_1$, $\alpha_2$, $\alpha_3$, $\alpha_4$, as, $\alpha_6$ and $\alpha_7$ are parameters used to establish a primary relationship among the objectives. Composite values for each composite function in the plurality of composite function can be calculated for an individual based on the objective values for each objective in the multi-objective optimization problem. For example, if the values of $\alpha_1$, $\alpha_2$, $\alpha_3$, $\alpha_4$, $\alpha_5$, $\alpha_6$ and $\alpha_7$ are 1000, 10, 1, 1, 10, 1 and 10 respectively, and if the objective value for objective $\alpha$ is 1, the objective value for objective b is 5 and the objective value of objective c is 10, then the composite values for composite functions 1, 2 and 3 are 1060, 51 and 101 respectively.

In the single-objective optimization problem, the superiority of an individual over other individuals is easily determined by comparing their objective values. In some multi-objective optimization embodiments, the quality of an individual can be determined by the dominance of said individual over other individuals in the multi-objective search space. In some embodiments, a first individual is said to dominate over a second individual if (i) at least one composite value of the first individual is greater than the composite value of the second individual for the corresponding composite function, and (ii) none of the composite values of the first individual is lower than the corresponding composite values of the second individual.

Many modifications and variations of the definition of dominance will be apparent to practitioners skilled in this art. For example, in another embodiment, at least two of the composite values of one individual must be higher than the corresponding composite values of another individual in order to conclude that the first individual dominates over the second individual.

Example Embodiment

FIG. 1 is an overall diagram of an embodiment of a data mining system incorporating features of the invention. The system is divided into three portions, a training system 110, a production system 112, and a controlled system 128. The training system 110 interacts with a database 114 containing training data, as well as with another database 116 containing the candidate individual pool. As used herein, the term "database" does not necessarily imply any unity of structure. For example, two or more separate databases, when considered together, still constitute a "database" as that term is used herein. The training system 110 operates according to a plurality of composite functions 140, which indicate to the training system 110 how to measure the composite values of an individual. The plurality of composite functions 140 also defines the search space for individuals with respect to the multiple objectives 130 in the data mining environment. The training system 110 attempts to optimize for individuals that have the greatest dominance over other individuals in the defined search space. Whether a certain individual dominates over other is determined by a specified dominance filter 120.

The production system 112 operates according to a production individual population in another database 122. The production system 112 applies these individuals to production data 124, and produces outputs 126, which may be action signals or recommendations. In the healthcare domain, the production data 124 may be current, real-time or near-real-time patient data, and the outputs 126 of the production system 112 may be a suggested diagnosis or treatment regimen that one or more of the individuals in production individual population 122 outputs in response to the production data 124. The production individual population 122 is harvested from the training system 110 once or at intervals, depending on the embodiment.

The controlled system 128 is a system that is controlled automatically by the signals 126 from the production system. Depending on the application environment, the controlled system 128 may include mechanical systems such as engines, air-conditioners, refrigerators, electric motors, robots, milling equipment, construction equipment, or a manufacturing plant, or other computer systems, or an output display to inform a user of a recommendation or diagnosis.

While the embodiment of FIG. 1 operates the training system separately from the production system, aspects of the invention also apply to so-called "online" learning systems in which the training system and the production system are one. That is, training is performed on actual production data, and the outputs of the candidate individuals are actually used to operate the controlled system 128, even though the candidate individuals may not yet have been fully vetted. Candidate individuals are evaluated on actual feedback from the use of their outputs by the controlled system 128. Such a system may never harvest individuals for use in production, because they are already being used in production.

In one embodiment, the individuals in candidate pool 116 are stored and managed by conventional database management systems (DBMS), and are accessed using SQL statements. New individuals can be inserted into the candidate pool 116 using the SQL "insert" statement, and individuals being discarded can be deleted using the SQL "delete" statement. In another embodiment, the individuals in candidate pool 116 are stored in a linked list. In such an embodiment insertion of a new individual can be accomplished by writing its contents into an element in a free list, and then linking the element into the main linked list. Discarding of individuals involves unlinking them from the main linked list and re-linking them into the free list. Discarding causes an individual to be removed from competition, but in some embodiments, information about the individual may be recorded or logged for other purposes.

Figure 2:
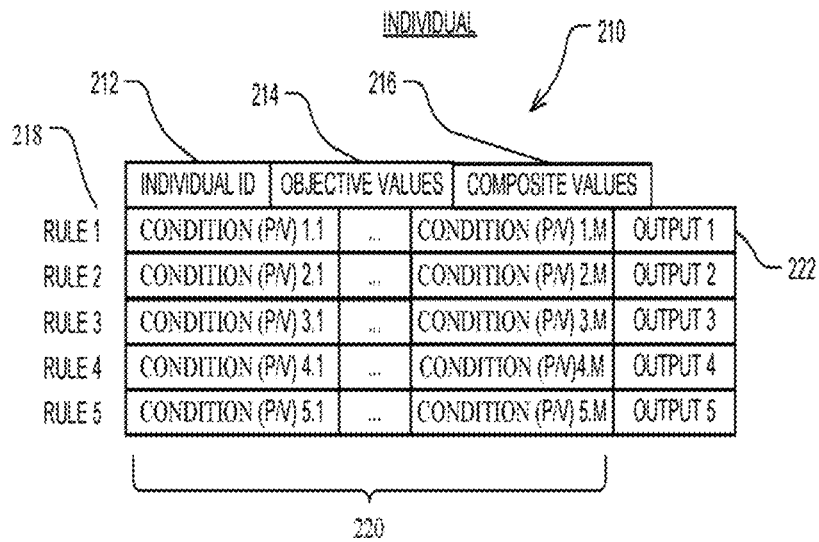
FIG. 2 is a symbolic drawing of an individual in either the candidate individual pool or the production individual population of FIG. 1, according to an embodiment of the invention.

FIG. 2 is a symbolic drawing of an individual 210 in either the candidate individual pool 116 or the production individual population 122. As used herein, an "individual" created by procreation is considered herein to constitute a different individual than its parents, even though it retains some of its parents' genetic material. In this embodiment, the individual identifies an ID 212. Individuals in the candidate individual pool 116 also identify the individual's objective values 214 (one for each objective 130). Alternatively, or additionally, each individual in the candidate pool 116 identifies the composite values 216 for each composite function 140 defined for the multi-objective data mining environment. Some embodiments may also define a single overall fitness estimate for each individual, and that value, too, may be stored as part of the individual.

In the embodiment of FIG. 2, individual 210 also includes one or more "rules" 218, each of which contains one or more conditions 220 and an output 222 to be asserted if all the conditions in a given sample are true. During procreation, any of the conditions or any of the outputs may be altered, or even entire rules may be replaced. As used herein, a "result" of an individual is the combination of outputs produced by an individual in response to a single data sample (either during training or in production), and the "performance" of an individual with respect to an objective is a measure of how well the "result" satisfied that objective on that single sample.

A rule is a conjunctive list of conditions in association with an output. In the embodiment of FIG. 2, the individual's conditions are all specified as parameter/value ("P/V") pairs. That is, if in the current sample, the specified parameter has the specified value (or range of values), then the condition is true. Another embodiment can also include conditions which are themselves conditioned on other items (such as other conditions in the rule or in a different rule or the result of another entire one of the rules). Yet another embodiment can also include conditions or rules which are specified procedurally rather than as P/V pairs. Many other variations will be apparent.

In a healthcare embodiment, an individual can be thought of as a set of rules predicting a patient's future state, given the patient's current and past states. In an embodiment, the set of rules may classify a patient's current state based on current and past states. The parameters on which the rules are based can be a patient's vital signs, and past treatment and medication history, for example. An example rule is as follows:

condition 1.1: pulse[t]>=120
condition 1.2: blood pressure[t−1]>=120
condition 1.3: blood pressure[t−6]<90 Output: high blood pressure related event
If condition 1.1 and condition 1.2 and condition 1.3, then Output.

The training data is arranged in the database 114 as a set of samples, each with parameters and their values, as well as sufficient information to determine a result that can be compared with an assertion made by an individual on the values in the sample. In one embodiment, the output is explicit, for example, a number set out explicitly in association with the sample. In such an embodiment, the objective values can be dependent upon the number of samples for which the individual's output matches the result of the sample. In another embodiment, such as in the healthcare embodiment, the result may not be present in the test data itself, but rather derivable from the test data. For example, the sample may include the vital signs of a patient throughout a day, and the training system 110 must hypothetically evaluate recommendations made by the individual throughout the day in order to determine whether and to what extent the individual has been successful in its objective of accurately diagnosing any ailment. Note that whereas in the embodiment of FIG. 2 the individuals are expressed in terms of rules, that is not required in all embodiments. In another embodiment, an individual might, for example, be expressed in terms of a vector of floating point numbers. Many other embodiments will be apparent to the skilled reader. In general, as used herein, individuals merely identify a potential solution to the problem provided to the system for solving.

Figure 3:
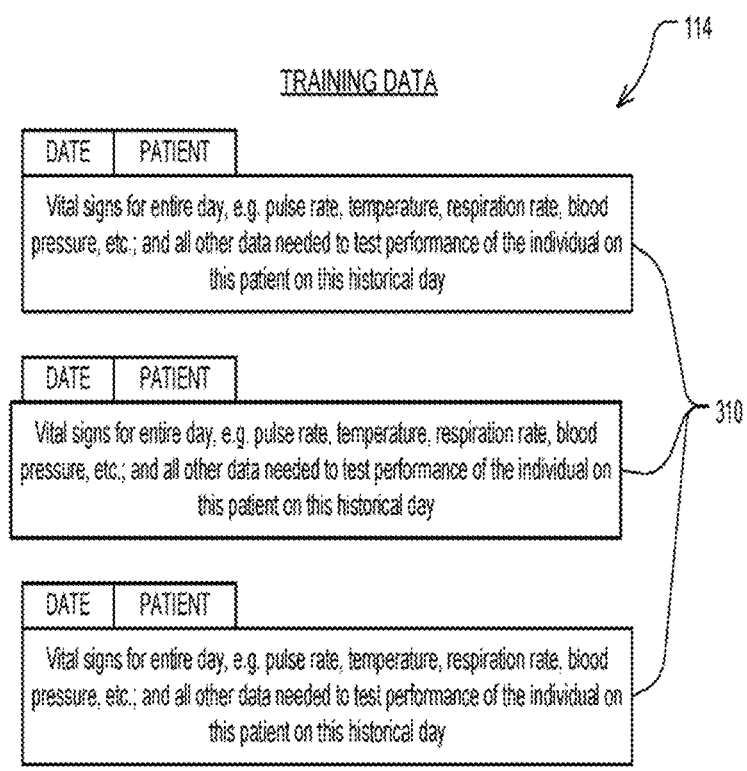
FIG. 3 is a symbolic drawing indicating how the training data database is organized, according to an embodiment of the invention.

FIG. 3 is a symbolic drawing indicating how the training data can be organized in the database 114. The illustration in FIG. 3 is for the healthcare embodiment, and it will be understood how it can be modified for use in other environments. Referring to FIG. 3, three samples 310 are shown. Each sample includes a historical date, an identification of a particular patient, and raw clinical data for that patient on that entire trading day, e.g., pulse rate, temperature, respiration rate, blood pressure, etc.; and all other data needed to test performance of the individual's success in achieving each of the objectives for this patient on this historical day. For example, the three samples of training data 310 could represent three days of clinical data, each sample representing one day of the same patient. Alternatively, the three samples could represent one day of clinical data for each of three patients. Any combination thereof may be used.

Training System

Figure 4:
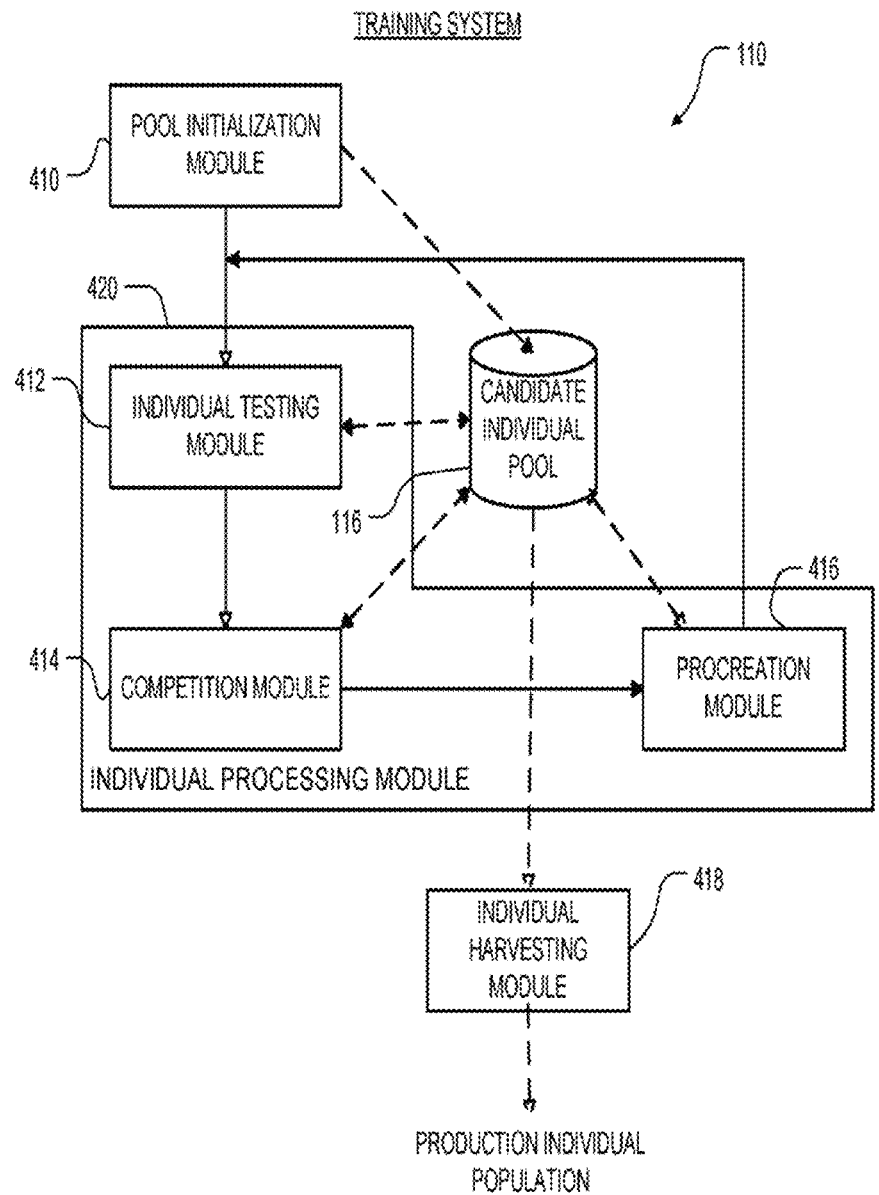
FIG. 4 illustrates modules that can be used to implement the functionality of the training system in FIG. 1, according to an embodiment of the invention.

FIG. 4 illustrates various modules that can be used to implement the functionality of training system 110 (FIG. 1). Candidate individual pool 116 is also shown in the drawing. Solid lines indicate process flow, and broken lines indicate data flow. The modules can be implemented in hardware or software, and need not be divided up in precisely the same blocks as shown in FIG. 4. Some can also be implemented on different processors or computers or spread among a number of different processors or computers. In addition, it will be appreciated that some of the modules can be combined, operated in parallel or in a different sequence than that shown in FIG. 4 without affecting the functions achieved. Also as used herein, the term "module" can include "sub-modules," which themselves can be considered herein to constitute modules. In particular, the individual testing module 412, competition module 414, and procreation module 416 are also considered herein to be sub-modules of an individual pool processor module 420. The blocks in FIG. 4 are designated as modules can also be thought of as flow-chart steps in a method.

Referring to FIG. 4, the candidate individual pool 116 is initialized by pool initialization module 410, which creates an initial set of candidate individuals in the individual pool 116. These individuals can be created randomly, or in some embodiments, a priori knowledge is used to seed the first generation. At the start, all individuals are initialized with objective values and composite values that are undefined.

Individual testing module 412 then proceeds to test the population in the individual pool 116 on the training data 114. Only a subset of the population in the individual pool 116 is tested at this point. As used herein, the term "subset," unless otherwise qualified, includes both proper and improper subsets as well as the null set. Each individual in the subset undergoes a battery of tests or trials on the training data 114, each trial testing the individual on one sample 310. In one embodiment, each battery might consist of only a single trial. Preferably, however, a battery of tests is much larger, for example on the order of 1000 trials. Note there is no requirement that all individuals undergo the same number of trials. Note also that in an online learning embodiment, "testing" of an individual may involve using the individual to control the controlled system 128, and receiving any resulting feedback.

After the tests, the individual testing module 412 updates the objective values associated with each of the objectives and the composite values for each of the composite functions for the individuals tested. In an embodiment, each of the objective values may be an average of the results of all trials of the individual for the specific objective. In an embodiment, each of the composite values may be an average of the corresponding composite function values based on the results of all trials of the individual. In an embodiment, each of the composite values may be calculated as the corresponding composite function evaluated at the individual's average objective values.

Once the objective values and composite values are updated in the candidate individual pool for each tested individual, the competition module 414 performs competition among individuals and may discard some individuals, leaving an elitist pool of candidate individuals. More detail about the competition process is provided below. After the candidate individual pool 116 has been updated, a procreation module 416 selects from the elitist pool a random subset of individuals from which to evolve new individuals. Any conventional or future-developed technique can be used for procreation. In an embodiment, conditions, outputs, or rules from parent individuals are combined in various ways to form child individuals, and then, occasionally, they are mutated. The combination process, for example, may include crossover—i.e., exchanging conditions, outputs, or entire rules between parent individuals to form child individuals. New individuals created through procreation begin with objective values and composite values that are undefined (i.e. indicate that they have not yet been assigned). These individuals are placed in the individual pool 116. Preferably, after new individuals are created by combination and/or mutation, the parent individuals are retained. In this case, the parent individuals also retain their objective values and composite values. In another embodiment, the parent individuals are discarded.

After procreation, individual testing module 412 operates again on the updated individual pool 116. The process continues repeatedly.

Individuals can be harvested for use by production system 112. Individual harvesting module 418 retrieves individuals for that purpose. In one embodiment, individual harvesting module 418 retrieves individuals periodically, whereas in another embodiment it retrieves individuals only in response to user input. Individual harvesting module 418 can apply certain selection criteria as well in order to choose desirable individuals. For example, in one embodiment it selects only individuals that are not dominated by any other individuals in the pool. The individuals may also undergo further validation as part of this further selection process, by testing on historical data not part of training data 114. The individuals selected by the individual harvesting module 418 are written to the production individual population database for use by production system 112 as previously described. In an online learning embodiment, there may be no separate harvesting module since the candidate individuals essentially are already in production.

The competition module 414 utilizes the dominance filter 120 to select a first set of individuals. In one embodiment, the competition module 414 may select all individuals currently in the candidate pool 116, to be included in the first set of individuals. In another embodiment, the competition module 414 may select a predetermined number of individuals currently in the candidate pool 116 to be included in the first set of individuals. The competition module 414 then selects a final set of individuals from the first set of individuals in dependence upon relative novelty and relative diversity among the individuals in the first set of individuals. In one embodiment, any individual not included in the final set of individuals is discarded from the candidate individual pool 116. The individual processing module 420 uses the final set of individuals for procreating new individuals and adding them to the pool of candidate individuals.

Figure 5B:
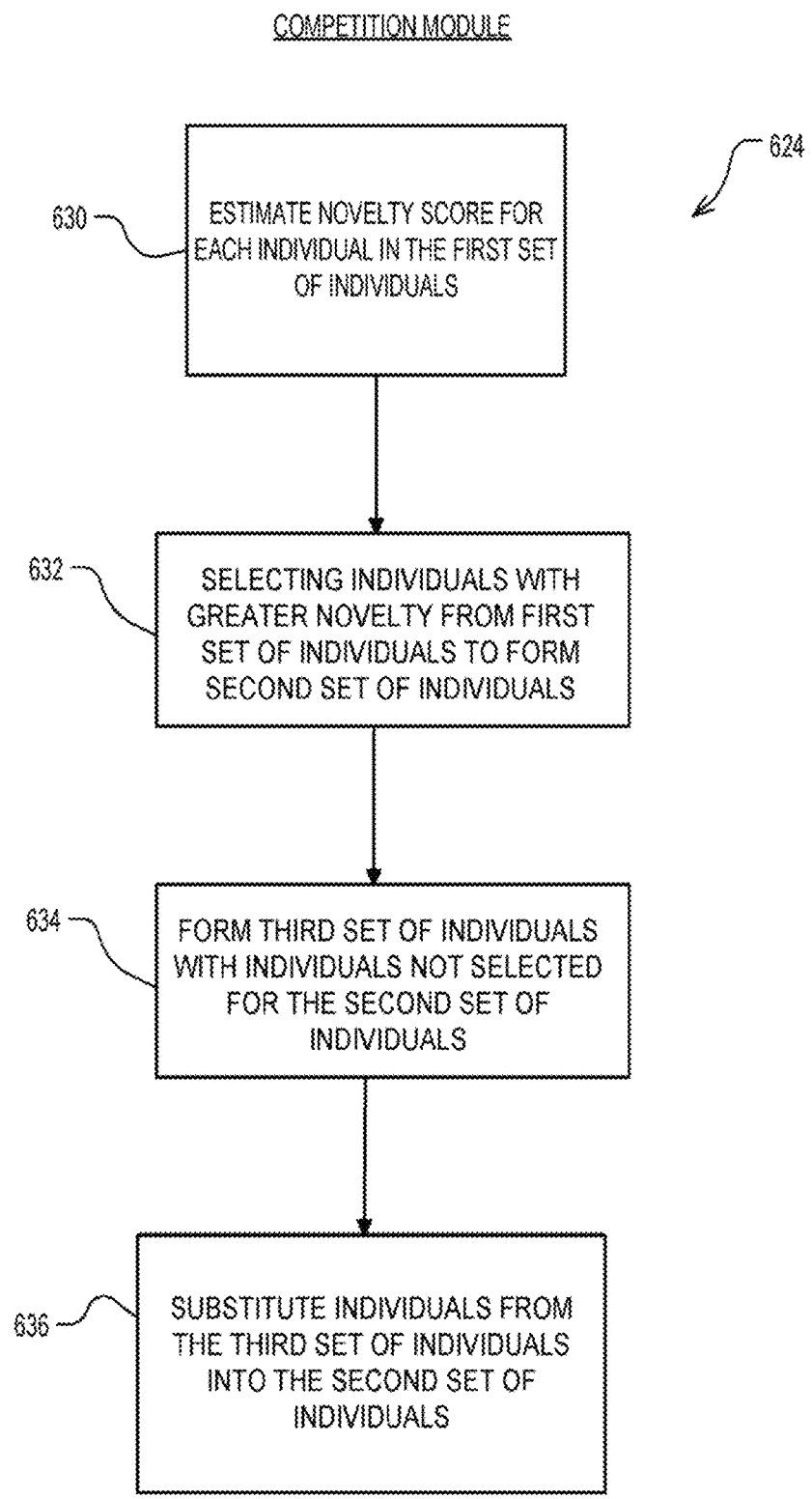
Figure 5C:
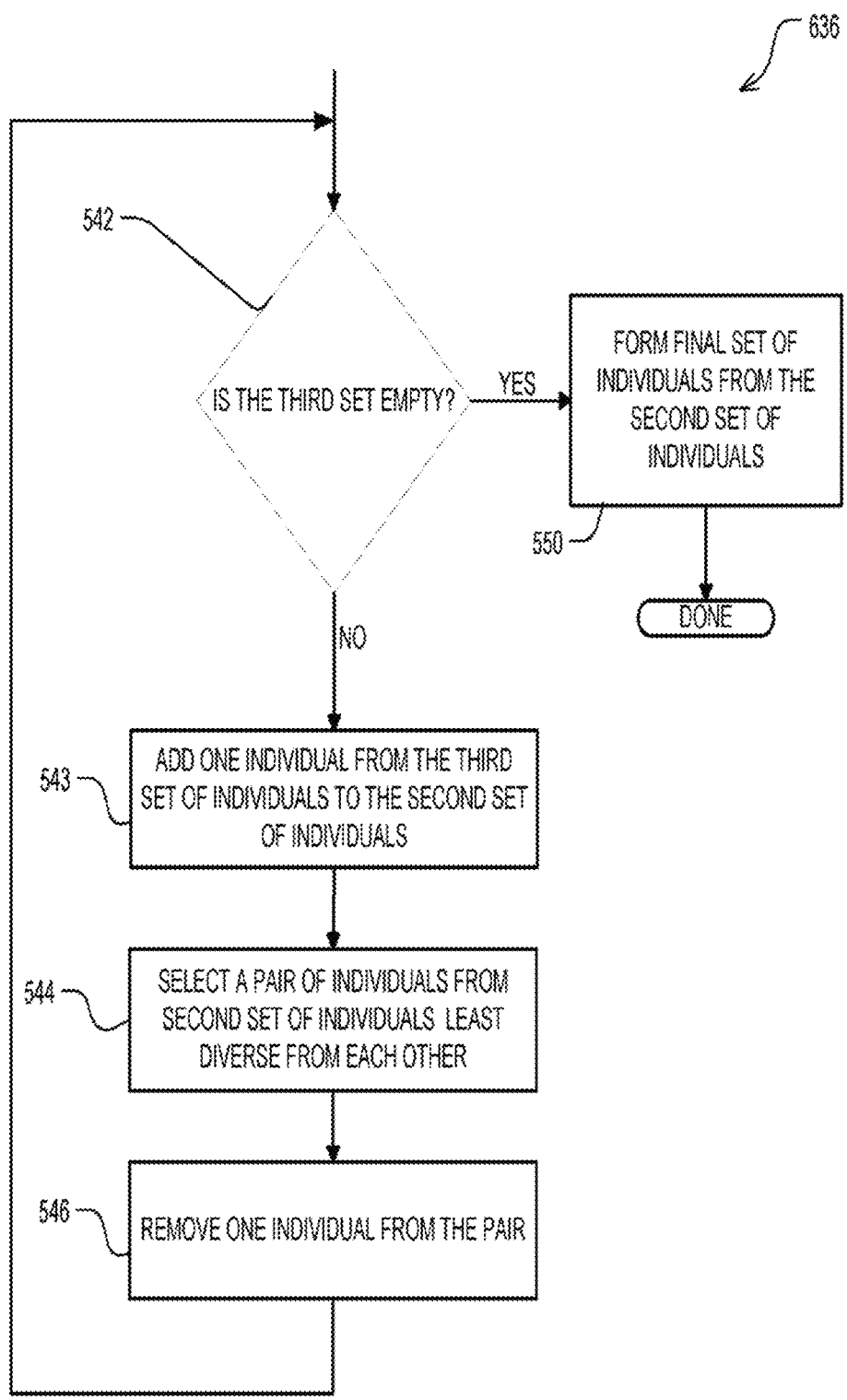

FIG. 5 (consisting of FIGS. 5A, 5B and 5C) illustrates a method of operation of competition module 414. In the embodiment of FIG. 5, the competition module 414 selects individuals from the candidate individual pool 116 to be included in the first set of individuals by using a dominance filter at step 521. These executions of competition module 414 are sometimes referred to herein as competition "events," and each comparison made between the dominance estimate of one individual and that of another by the dominance filter is sometimes referred to herein as a comparison "instance." As compared to a conventional multi-objective search, the optimization of composite functions instead of raw objective values tends to favor individuals for the first set of individuals that are in a focused area of objective space (a multi-dimensional space in which each orthogonal axis represents a different one of the objectives). Overall diversity of behavior among the individuals in the first set of individuals may be reduced, however.

More specifically, it will be appreciated that different individuals, even if they have the same objective values (i.e. occupy the same position in objective space), might exhibit entirely different behavior in reaching those objective values. For example, if an objective of the search is the time that a robot requires to reach a destination, then two individuals might cause the robot to reach the destination in the same amount of time. But one may achieve that time by causing the robot to take many short steps, whereas the other may achieve that time by causing the robot to take fewer long steps. These two individuals can be said to have a certain amount of diversity in behavior, even if not in fitness. To evaluate diversity of behavior, a "behavior space" may be defined in which multiple aspects of an individual's behavior are identified, and each aspect is represented in behavior space by a respective orthogonal axis. An individual's location in behavior space then is given by the vector of its values in each of the behavioral aspects. It can thus be appreciated that even if a set of individuals appear diverse in objective space, they may lack diversity in behavior space, or vice-versa.

In one embodiment, the first set of individuals is the final set of individuals, the elitists which proceed to the procreation module. In another embodiment, however, the process continues in an effort to ensure diversity in behavior space. Thus in step 524, the competition module 414 selects a final set of individuals from the first set of individuals. The final set of individuals is generally smaller than the first set of individuals. Diversity in behavior can be encouraged in the focused area of search by utilizing a relative novelty measure and a relative diversity measure among the individuals in the first set of individuals to select the final set of individuals. In step 524, the competition module 414 can further discard from the candidate individual pool all individuals in the pool that are not in the final set of individuals. Therefore, after discarding, the candidate individual pool contains the individuals from the final set of individuals.

In one embodiment, selection of the first set of individuals in module 521 uses Pareto-optimization. The module selects individuals from the candidate individual pool that are not dominated by any other individuals in the pool to form the first set of individuals. In another embodiment, the competition module 414 may select a predetermined number of individuals from the candidate individual pool, such that the individuals not present in the first set of individuals have the least dominance over the individuals in the first set of individuals. In order to determine whether an individual is dominated by other individuals in the pool of candidate individuals, the dominance of said individual over every other individual in the candidate individual pool is evaluated. A first individual in the pool dominates over a second individual in the pool if the composite value of the first individual is greater than composite value of the second individual for at least one corresponding composite function, and the composite value of the first individual is not lower than composite value of the second individual for any other composite functions. For example, an individual x has composites values of 23, 44 and 20 for composite functions 1, 2 and 3 respectively, while an individual y has composite values of 10, 10 and 10. Individual x clearly dominates individual y as individual x has higher composite values than individual y for all three composite functions. If individual y has composites values of 23, 34 and 20 for composite functions 1, 2 and 3 respectively, individual x still dominates individual y as individual x has a higher composite value than individual y for at least one composite function (composite function 2), while the composite values of individual x for the other two composite functions (composite function 1 and composite function 3) are not lower than composite value of individual y for those two composite functions. If individual y has composites values of 23, 54 and 5 for composite functions 1, 2 and 3 respectively, individual x no longer dominates individual y even though individual x has a higher composite value than individual y for at least one composite function (composite function 3). The composite value of individual x for composite function 2 is lower than the composite value of individual y for the corresponding composite functions. Some methods to perform Pareto-optimization are described in the above-incorporated NSGA-11 paper.

FIG. 5B illustrates a method by which the competition module 414 selects a final set of individuals from the second set of individuals in dependence upon relative novelty and relative diversity among the individuals in the first set of individuals. At step 630, the competition module 414 estimates the average novelty score for each individual in the first set of individuals. In an embodiment, when individuals from the candidate individual pool are tested against a portion of the training data, a behavioral value of the individual is identified. As used herein, a "behavioral value" $b(x)$ of an individual x in a data mining environment is a vector or a scalar number resulting from the evaluation of the individual in the data mining environment, according to a predefined measure of its behavior. For example, for a robot navigating a maze, the predetermined measure of the robot's behavior of the robot may be a history of how the robot solves the task to get to its final destination, rather than the speed at which it reaches the final destination. In other words, the predetermined measure of the behavior of an individual captures a space that is expected to have practical benefits. As used herein, a "behavior difference" $d(b(x),b(y))$ between an individual x and an individual y is the distance between two individuals in the behavior space. The average novelty score of an individual $x_i$ can be estimated by summing the pairwise distance of its behavior vector to that of all the other individuals in the first set of individuals. Therefore, for the first set of individuals with n individuals, the average novelty score of individual $x_i$ can be estimated by $$\text{Average novelty score } (x_i) = \Sigma_{j=1}^{n} d(b(x_i), b(x_j)). \tag{4}$$

At step 632, the competition module 414 selects a predetermined number of individuals with greater novelty from the first set of individuals to form the second set of individuals. In some embodiments, individuals with the highest novelty score in the first set of individuals are selected to form the second set of individuals.

It is possible that step 632 may result in a cluster of solutions that are far from the rest of the crowd in behavior space, because they all have high novelty scores when compared to the others. Though not necessary in all embodiments, it might be good enough to keep only one representative from that behavioral cluster. In order to address this issue, at step 634, the competition module 414 forms a third set of individuals with the individuals in the first set of individuals not included in the second set of individuals. At step 636 the competition module 414 then substitutes individuals from the third set of individuals into the second set of individuals, one by one, in a manner that improves the behavioral diversity of the individuals in the second set of individuals, to form the final set of individuals.

FIG. 5C illustrates a method by which the competition module 414 substitutes individuals from the third set of individuals into the second set of individuals in a manner that improves the behavioral diversity of the individuals in the second set of individuals. At step 542, it is first determined whether the third set of individuals is empty. If not, then at step 543, the competition module 414 adds an individual from the third set of individuals to the second set of individuals, thereby reducing the size of the third set of individuals by one and increasing the size of the second set by one. At step 544, two individuals are selected from the second (now enlarged) set of individuals that have the smallest behavior difference. At step 546, one of these individuals is retained in the second set of individuals while the other is discarded. In one embodiment, the dominance filter 120 may be used to determine which individual among the two selected individuals dominate over the other. In another embodiment, overall fitness estimates of the two selected individuals may be used in order to choose which individual to discard. The individual with the lower fitness estimate is discarded. Obviously, many modifications and variations of filters will be apparent to practitioners skilled in this art that can be used to discard one individual from the two selected individuals. Discarding one of the individuals from the two individuals with the smallest behavior difference and adding an individual from the third set of individuals to the second set of individuals improves the diversity of individuals in the second set of individuals.

The procedure then returns to step 542, where it is again determined whether the size of the third set of individuals is zero. If yes, then the final set of individuals is formed from the second set of individuals. It can be seen that the combined procedures of FIGS. 5A, 5B, and 5C add to the formation of the final set of individuals by the competition module 414.

Note that whereas in FIG. 5C, an individual is added from the third subset into the second subset (step 543) before steps 544 and 546 remove an individual from a least diverse pair in the second set. In another embodiment, steps 544 and 546 may remove an individual from a least diverse pair in the second set before an individual is added from the third subset into the second subset. Other variations will be apparent. As with all flowcharts herein, it will be appreciated that many of the steps can be combined, performed in parallel or performed in a different sequence without affecting the functions achieved. In some cases, as the reader will appreciate, a re-arrangement of steps will achieve the same results only if certain other changes are made as well. In other cases, as the reader will appreciate, a re-arrangement of steps will achieve the same results only if certain conditions are satisfied. Furthermore, it will be appreciated that the flow charts herein show only steps that are pertinent to an understanding of the invention, and it will be understood that numerous additional steps for accomplishing other functions can be performed before, after and between those shown.

Computer Hardware

Figure 6:
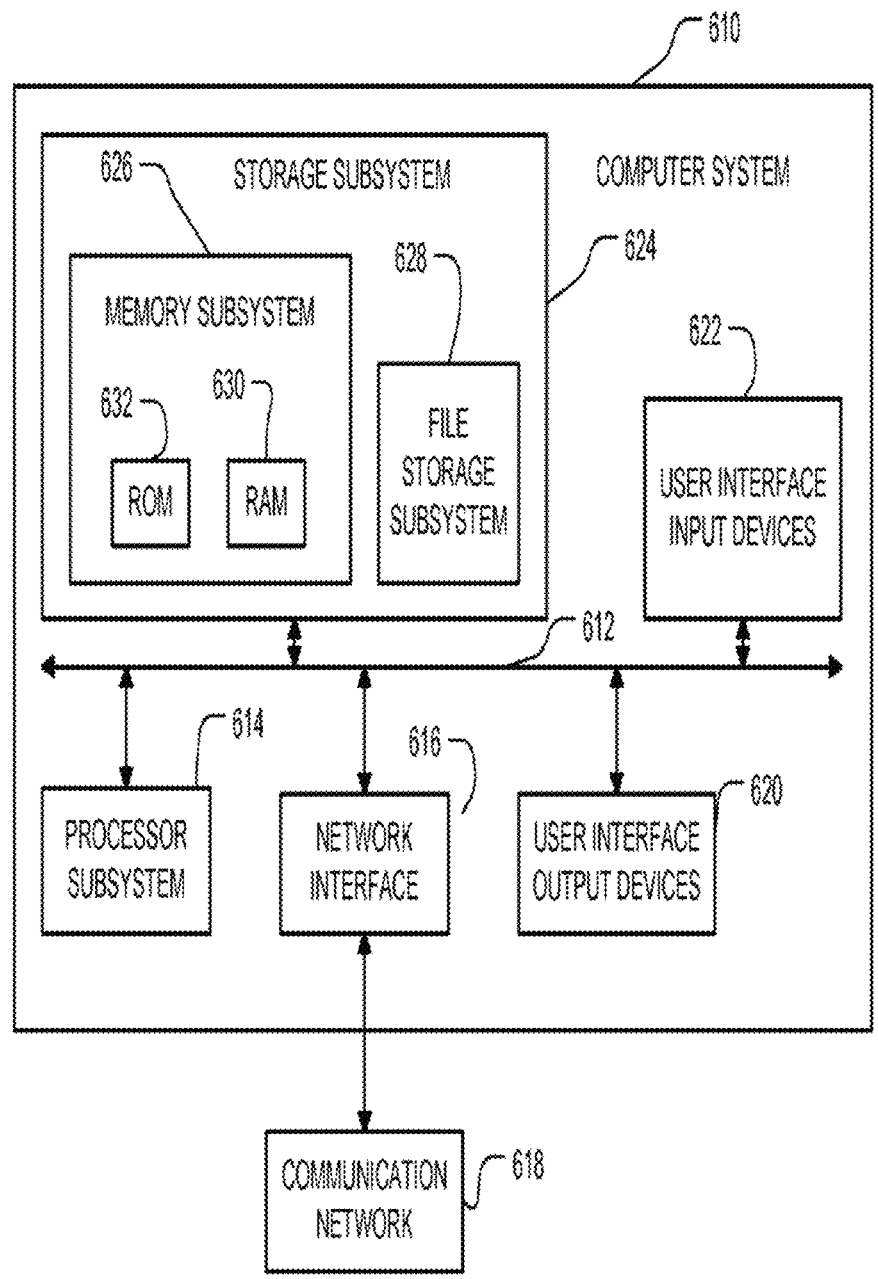
FIG. 6 is a simplified block diagram of a computer system that can be used to implement either or both of the training system or production system in FIG. 1, and/or the training server and clients in FIG. 7, according to an embodiment of the invention.

FIG. 6 is a simplified block diagram of a computer system 610 that can be used to implement training system 110, production system 126, or both. While FIGS. 1, 4, 5A, 5B, 5C, 7, 8 and 9 indicate individual components for carrying out specified operations, it will be appreciated that each component actually causes a computer system such as 610 to operate in the specified manner.

Computer system 610 typically includes a processor subsystem 614 which communicates with a number of peripheral devices via bus subsystem 612. These peripheral devices may include a storage subsystem 624, comprising a memory subsystem 626 and a file storage subsystem 628, user interface input devices 622, user interface output devices 620, and a network interface subsystem 616. The input and output devices allow user interaction with computer system 610. Network interface subsystem 616 provides an interface to outside networks, including an interface to communication network 618, and is coupled via communication network 618 to corresponding interface devices in other computer systems. Communication network 618 may comprise many interconnected computer systems and communication links. These communication links may be wireline links, optical links, wireless links, or any other mechanisms for communication of information. While in one embodiment, communication network 618 is the Internet, in other embodiments, communication network 618 may be any suitable computer network.

The physical hardware component of network interfaces are sometimes referred to as network interface cards (NICs), although they need not be in the form of cards: for instance they could be in the form of integrated circuits (ICs) and connectors fitted directly onto a motherboard, or in the form of macrocells fabricated on a single integrated circuit chip with other components of the computer system.

User interface input devices 622 may include a keyboard, pointing devices such as a mouse, trackball, touchpad, or graphics tablet, a scanner, a touch screen incorporated into the display, audio input devices such as voice recognition systems, microphones, and other types of input devices. In general, use of the term "input device" is intended to include all possible types of devices and ways to input information into computer system 610 or onto computer network 818.

User interface output devices 620 may include a display subsystem, a printer, a fax machine, or nonvisual displays such as audio output devices. The display subsystem may include a cathode ray tube (CRT), a flat-panel device such as a liquid crystal display (LCD), a projection device, or some other mechanism for creating a visible image. The display subsystem may also provide a nonvisual display such as via audio output devices. In general, use of the term "output device" is intended to include all possible types of devices and ways to output information from computer system 610 to the user or to another machine or computer system. In particular, an output device of the computer system 610 on which production system 112 is implemented, may include a visual output informing a user of action recommendations made by the system, or may include a communication device for communicating action signals directly to the controlled system 128. Additionally or alternatively, the communication network 618 may communicate action signals to the controlled system 128. In the health embodiment, for example, the communication network 618 transmits message signals to a computer system in a hospital or a doctor's office.

Storage subsystem 624 stores the basic programming and data constructs that provide the functionality of certain embodiments of the present invention. For example, the various modules implementing the functionality of certain embodiments of the invention may be stored in storage subsystem 624. These software modules are generally executed by processor subsystem 614. Storage subsystem 624 also stores the candidate individual pool 116, the training database 114, and/or the production individual population 122. Alternatively, one or more of such databases can be physically located elsewhere, and made accessible to the computer system 610 via the communication network 618.

Memory subsystem 626 typically includes a number of memories including a main random access memory (RAM) 630 for storage of instructions and data during program execution and a read-only memory (ROM) 632 in which fixed instructions are stored. File storage subsystem 628 provides persistent storage for program and data files, and may include a hard disk drive, a floppy disk drive along with associated removable media, a CD ROM drive, an optical drive, or removable media cartridges. The databases and modules implementing the functionality of certain embodiments of the invention may have been provided on a computer readable medium such as one or more CD-ROMs, and may be stored by file storage subsystem 628. The host memory 626 contains, among other things, computer instructions which, when executed by the processor subsystem 614, cause the computer system to operate or perform functions as described herein. As used herein, processes and software that are said to run in or on "the host" or "the computer," execute on the processor subsystem 614 in response to computer instructions and data in the host memory subsystem 626 including any other local or remote storage for such instructions and data.

Bus subsystem 612 provides a mechanism for letting the various components and subsystems of computer system 610 communicate with each other as intended. Although bus subsystem 612 is shown schematically as a single bus, alternative embodiments of the bus subsystem may use multiple busses.

Computer system 610 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 610 depicted in FIG. 6 is intended only as a specific example for purposes of illustrating the preferred embodiments of the present invention. Many other configurations of computer system 610 are possible having more or less components than the computer system depicted in FIG. 6.

Client/Server Embodiment

In some environments, the training data used to evaluate an individual's fitness can be voluminous. Therefore, even with modern high processing power and large memory capacity computers, achieving quality results within a reasonable time is often not feasible on a single machine. A large individual pool also requires a large memory and high processing power. In one embodiment, therefore, a client/server model is used to provide scaling in order to achieve high-quality evaluation results within a reasonable time period. Scaling is carried out in two dimensions, namely in pool size as well as in the evaluation of the same individual to generate a more diverse individual pool so as to increase the probability of finding fitter individuals. In the client/server embodiment, the individual pool is distributed over a multitude of clients for evaluation. Each client maintains its own client-centric individual pool using data from training database 114, which it may receive in bulk or periodically on a sustained and continuing basis. Individuals that satisfy one or more predefined conditions on a client computer are transmitted to the server to form part of a server-centric individual pool.

Distributed processing of individuals also may be used to increase the speed of evaluation of a given individual. To achieve this, individuals that are received by the server but have not yet been tested on a certain number of samples, or have not yet met one or more predefined conditions, may be sent back from the server to a multitude of clients for further evaluation. The evaluation result achieved by the clients (alternatively called herein a partial evaluation) for an individual is transferred back to the server. The server merges the partial evaluation results of an individual with that individual's fitness estimate at the time it was sent to the clients to arrive at updated objective values and/or composite values for that individual in the server-centric individual pool. For example, assume that an individual has been tested on 500 samples and is sent from the server to, for example, two clients each instructed to test the individual on 100 additional samples. Accordingly, each client further tests the individual on the additional 100 samples and reports its own client-centric objective values and/or composite values to the server. The server combines these two estimates with the individual's objective values and/or composite values at the time it was sent to the two clients to calculate updated server-centric objective values and/or composite values for the individual. The combined results represent the individual's updated objective values and/or composite values evaluated over 700 days. A distributed system, in accordance with the present invention, is thus highly scalable in evaluating its individuals.

Advantageously, clients are enabled to perform individual procreation locally, thereby improving the quality of their individuals. Each client is a self-contained evolution device, not only evaluating the individuals in its own pool but also creating a new generation of individuals and moving the evolutionary process forward locally. Thus clients maintain their own client-centric individual pool which need not match each other's or the server-centric individual pool. Since the clients continue to advance with their own local evolutionary process, their processing power is not wasted even if they are not in constant communication with the server. Once communication is reestablished with the server, clients can send in their individuals to the server and receive additional individuals from the server for further testing.

Figure 7:
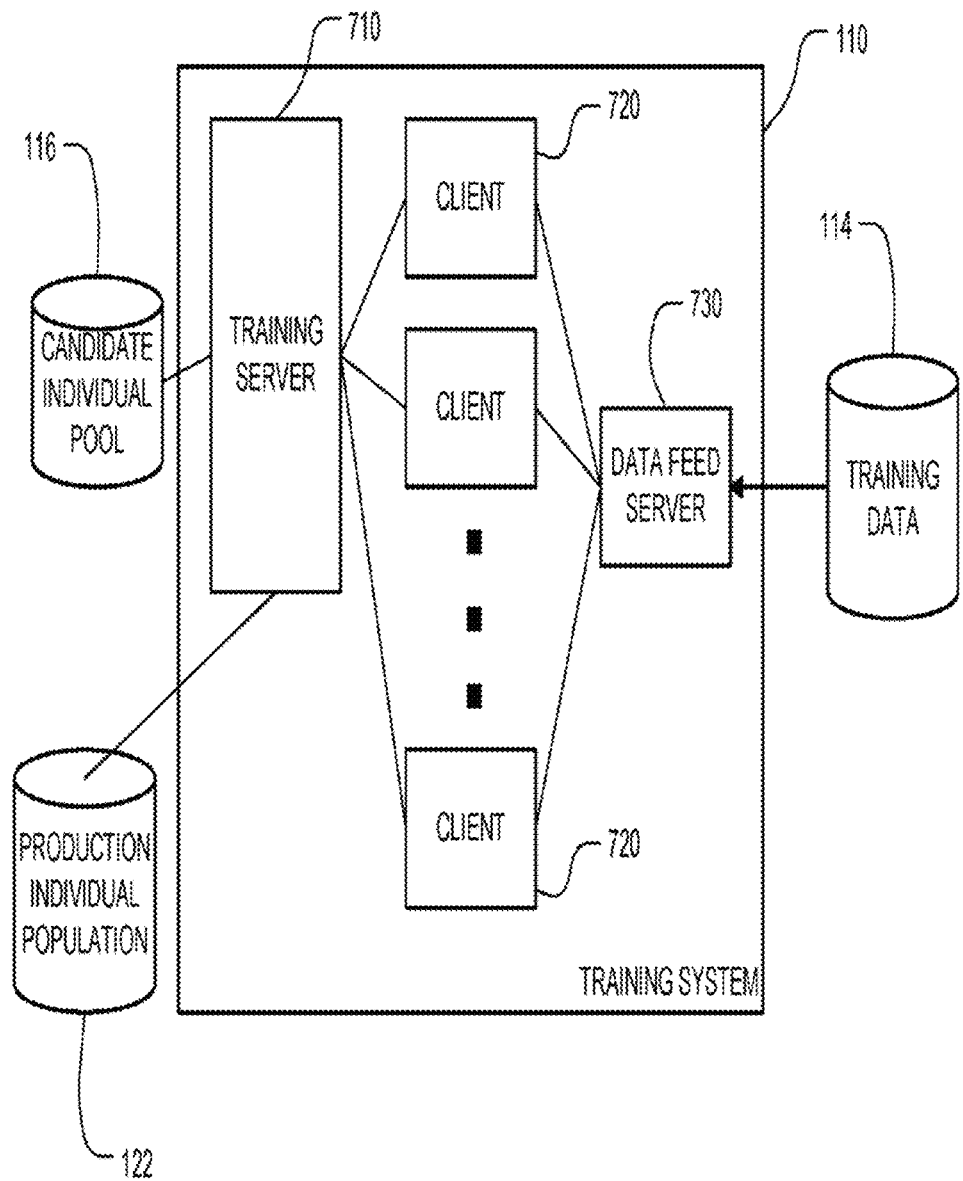
FIG. 7 is a high-level block diagram of an example embodiment of the training system of FIG. 1 using a network computing system.

FIG. 7 is a high-level block diagram of an example embodiment of training system 110 implemented using a network computing system. The training system 110 includes a plurality of client computers 720 (sometimes referred to herein simply as "clients") and a training server computer 710. Server 710 may itself be a central or a distributed server. A client computer 720 may be a laptop computer, a desktop computer, a cellular/VoiP handheld computer or smart phone, a tablet computer, distributed computer, or the like. An example system may have hundreds of thousands of clients. In an embodiment, the training server and/or each of the client computers can have the structure of FIG. 6, or any of its variations as described above. The client computers 720 communicate with the training server 710 to receive individuals for testing, and to report tested individuals back to the training server 710. The training server 710 maintains a server-centric candidate individual pool 116. New individuals are created by clients, both during initialization and by procreation, and they are not reported to the training server 710 until they have been tested on sufficient numbers of samples. The number of individuals created by the clients 720 may vary depending on the memory size and the CPU processing power of the client. For example, in one embodiment, a client may have 1000 individuals for evaluation. Each client computer 720 further has a communication port to access one or more data feed servers 730, which retrieve and forward training samples from the training database 114 to the client computers 720. Alternatively, although not shown, the training samples may be supplied from data feed server 730 to the clients 720 via the training server 710.

Figure 8:
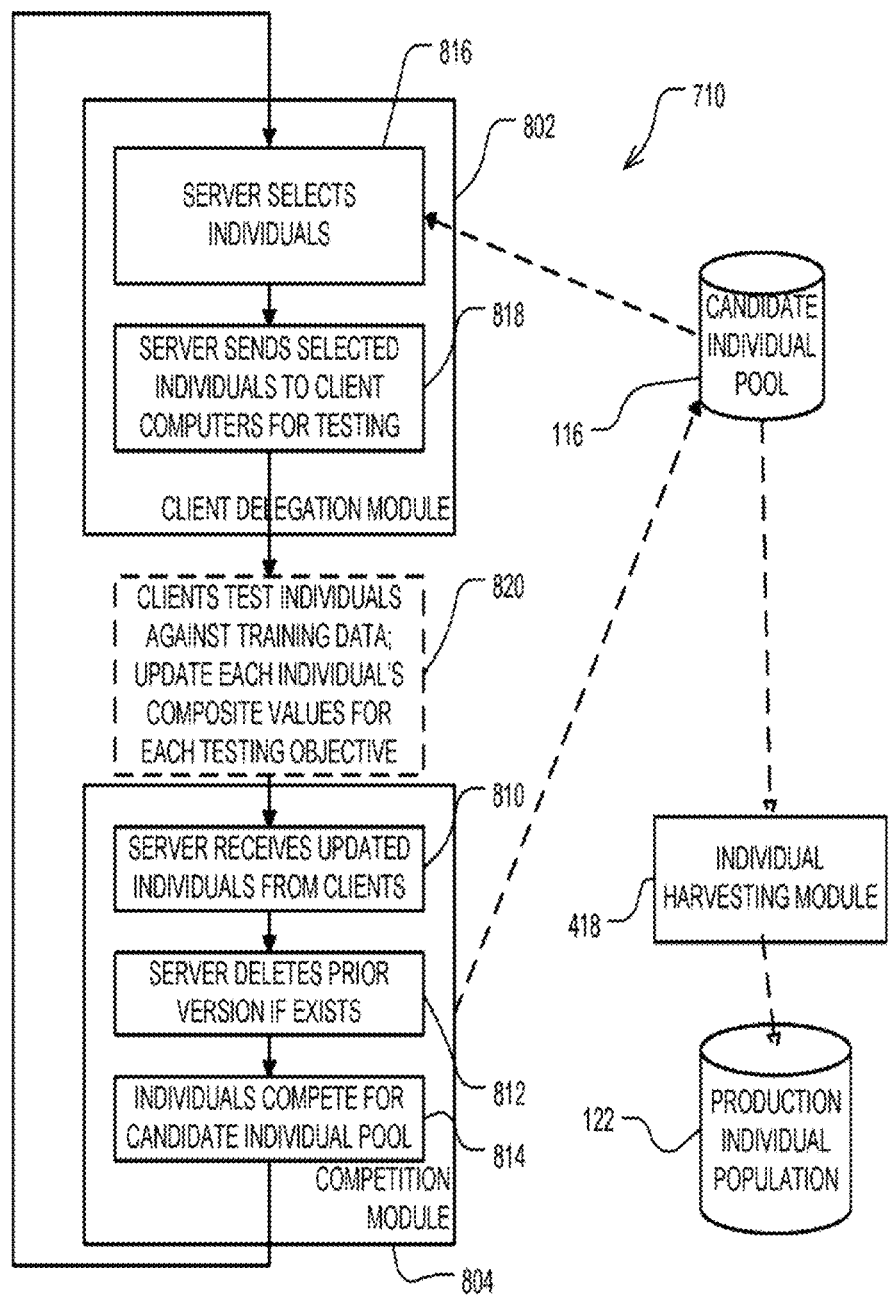
FIG. 8 illustrates modules that can be used to implement the functionality of training server of FIG. 7, according to an embodiment of the invention.

FIG. 8 illustrates various modules that can be used to implement the functionality of training server 710 (FIG. 7). Candidate individual pool 116 and production individual population database 122 are also shown in the drawing. As in the embodiment of FIG. 4, solid lines in FIG. 8 indicate process flow, and broken lines indicate data flow. The implementation variations mentioned above with respect to the embodiment of FIG. 4 apply to FIG. 8 as well.

In the client/server model enforces competition within its own server-centric candidate individual pool 116 when individuals are returned from clients. FIG. 8 illustrates various modules that can be used to implement the functionality of training server 710. Like the embodiment of FIG. 4, the training server 710 includes a competition module 804. It also includes individual harvesting module 418, which may be same as in FIG. 4. It also includes individual testing and procreation functionality, but these are combined into a single client delegation module 802 in FIG. 8. The client delegation module 802 and the competition module 804 constitute two sub-modules in an individual pool processor module (not shown specifically in FIG. 8). The FIG. 8 embodiment does not include a pool initialization module in the sense of FIG. 4, since as mentioned, the clients initialize their own individual pools.

Referring to FIG. 8, in step 810, the competition module 804 receives individuals from one or more of the client computers 720. These individuals may arrive asynchronously, if and when client computers have them available to transmit. Some individuals previously sent out for testing may never return. Individuals may arrive individually, or in bunches. If an arriving individual is new to the training server 710 (and, in some embodiments, also if the arriving individual is already known to the training server 710). At various times determined by competition module 804, after at least one individual has arrived, competition module 804 proceeds to step 812 to begin a competition "event."

In step 812, competition module 804 determines whether each incoming individual is a new one or a return of an individual that the server previously sent out for testing. This determination can be made on the basis of individual IDs 212 (FIG. 2). If the latter, then the training server 710 merges the newly received copy of the individual into the prior version in the server-centric candidate individual pool 116. In one embodiment, the merging step involves merely replacing the prior copy of the individual in the candidate individual pool 116, with the one newly received. In a variation of that embodiment, replacing may involve merely updating the objective value and/or composite value of the prior copy of the individual in the server-centric candidate individual pool 116.

In step 814 the incoming individual (if new) or the updated individual (if merged) competes for its position in the candidate individual pool 116. The same variations and rules of competition apply here as they do for the competition module 414 in the server-only model. The dominance filter uses the composite values of the individuals to discard one or more individuals from the pool, as described in more detail with respect to FIGS. 5A, 5B, and 5C.

In the client delegation module 802, in step 816, the server 710 selects individuals from the candidate individual pool 116 and sends them out to one or more clients 720 for further testing (step 818). In one embodiment, the battery of trials that an individual is to undergo is dictated by the training server. In such an embodiment, the server-centric view of the battery is the same as the client-centric view of the battery. In another embodiment, the battery of trials that an individual is to undergo is left to the client to decide, and the client may perform more than one battery of trials on the individual before returning it to the server. In the latter embodiment, the client has its own client-centric view of a testing battery.

In step 820 the client machines 720 test the individuals against training data from the data feed server 730 and update each individual's objective values and/or composite values locally. Step 820 is shown in broken lines in FIG. 8 because it is performed by clients rather than training server 710. At various subsequent times, the server 710 again receives back updated individuals from the clients in step 810 and repeats the process of FIG. 8.

The operation of the client computers 720 is the same as that previously described with respect to FIG. 4, with the exception that individuals are provided both by the pool initialization module 410, as well as from the training server 710. The candidate individual pool 116 in a client computer 720 is client-centric and includes all candidate individuals being considered by the clients. Preferably the candidate individual pool 116 in the client computers 720 are implemented using linked lists, whereas the candidate individual pool in the server 710 is implemented using a DBMS, both as previously described.

Note that because of procreation on the client system 720, individuals may be sent up to the training server 710 which the training server 710 had never before seen. Such individuals are handled in step 814 by requiring them to compete for their position in the server-centric candidate individual pool 116 of the training server 710. Note further that because of competition in the client computer 720, some individuals that the training server 710 sent to the client computer 720 for further testing will never be returned to the training server 710. In this case, the prior copy of the individual, retained by the training server 710, remains in place in the candidate individual pool 116 of the training server 710 unless and until it is displaced through competition in the training server 710 (step 814). Still further, note that an individual retained in the training server 710 after it has also been sent to a client 720 for further testing, may become displaced and deleted from the candidate individual pool 116 in the training server 710 through competition in the training server 710 (step 814). In this case, if the same individual is returned by the client computer 720, the training server 710 simply ignores it.

Procreation

Figure 9:
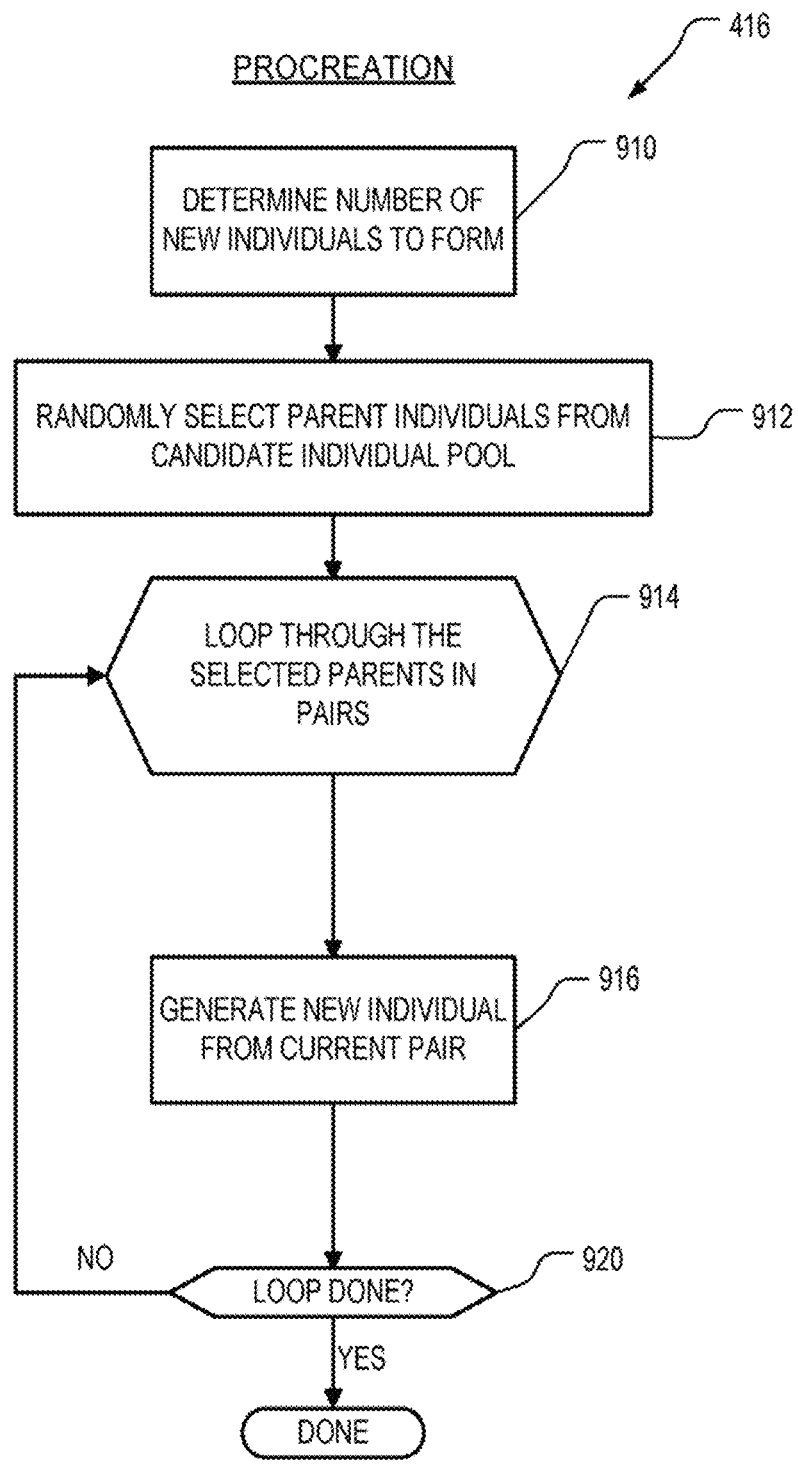
FIG. 9 is a flowchart of the procreation module in FIG. 4 according to an embodiment of the invention.

As mentioned, the procreation events that take place in procreation module 416. FIG. 9 is a flowchart illustrating an embodiment of this feature in more detail. Referring to FIG. 9, in step 910 the procreation module 416 determines how many new individuals to form in the current procreation event. For example, the number in one embodiment is calculated as 5% of the total number of individuals in the elitist pool.

In step 912, the procreation module 416 selects parent individuals from the candidate individual pool to use in the procreation process. Typically the individuals are selected randomly from throughout the candidate individual pool. In an experience layered embodiment of the candidate individual pool, individuals might be selected only from one or more layers of the elitist pool.

In step 914, the procreation module 416 begins a loop through the selected parents. Preferably parents are selected in pairs, and each new individual is formed from exactly two parents. In another embodiment, however, new individuals can be formed from a single parent individual, or from three or more parent individuals. In general, a "set" of one or more parents is used in the formation of each new individual by procreation.

In step 916, a new individual is formed from the current set of parents.

Any method of procreation can be used, such as those set forth elsewhere herein. In step 920, it is determined whether there are more sets of parents selected to procreate. If so, then procreation module 416 returns back to step 914 to generate another new individual by procreation.

Experimental Comparison

The efficacy of the composite novelty method discussed herein was tested against the following three pre-existing methods to address the problem of minimal sorting networks: Single Objective, Multi-Objective, Composite Multi-Objective. Initially, a general representation of the sorting network problem was developed. In this representation, sorting networks of n lines are seen as a sequence of two-leg comparators where each leg is connected to a different input line and the first leg is connected to a higher line than the second:

$$\{(f1,s1),(f2,s2),(f3,s3), \ldots ,(fc,sc)\} \qquad (5)$$

The number of layers can be determined from such a sequence by grouping successive comparators together into a layer until the next comparator would add a second connection to one of the lines in the same layer. With this representation, mutation and crossover operators amount to adding and removing a comparator, swapping two comparators, and crossing over the comparator sequences of two parents at a single point. It is noted that domain-specific techniques such as mathematically designing the prefix layers or utilizing certain symmetries which are known to those skilled in the art, were not used, but could be used in alternative implementations. Also of note, the experiment was standardized to a single machine (e.g., a multi-core desktop) with no cloud or distributed evolution benefits. To facilitate comparisons, a pool of one thousand individuals were evolved for a thousand generations with each of the four methods: Single Objective, Multi-Objective, Composite Multi-Objective and Composite Novelty.

With regards to the single-objective approach, note that correctness is part of the definition of a sorting network: Even if a network mishandles only one sample, it will not be useful. The number of layers can be considered the most important size objective because it determines the efficiency of a parallel implementation. A hierarchical composite objective can therefore be defined as:

$$\text{SingleFitness}(m,l,c)=10000m+100l+c \qquad (6)$$

where m, l, and c are the number of mistakes (unsorted samples), number of layers, and number of comparators, respectively. For this comparative experiment, solutions were limited to less than hundred layers and comparators, and therefore, the fitness is completely hierarchical (i.e. there is no folding).

In the multi-objective approach the same dimensions, i.e., the number of mistakes, layers, and comparators m, l, c, are used as three separate objectives. They are optimized by the NSGA-II algorithm (Deb et al. 2002) with selection percentage of 10%. This approach may discover solutions with just a single layer, or a single comparator, since they qualify for the Pareto front. Therefore, diversity is increased compared to the single-objective method, but not necessarily helpful diversity.

In order to construct composite axes, each objective was augmented with sensitivity to the other objectives:

$$\text{Composite1}(m,l,c)=10000m+100l+c, \qquad (7)$$

$$\text{Composite2}(m,l)=\alpha1 m+\alpha2 l, \qquad (8)$$

$$\text{Composite3}(m,c)=\alpha3 m+\alpha4 c \qquad (9)$$

The primary composite objective (7), which will replace the mistake axis, is the same hierarchical fitness used in the single-objective approach. It discourages evolution from constructing correct networks that are extremely large. The second objective (8), with $\alpha2=10$, primarily encourages evolution to look for solutions with a small number of layers. A much smaller cost of mistakes, with $\alpha1=1$, helps prevent useless single-layer networks from appearing in the population. Similarly, the third objective (9), with $\alpha3=1$ and $\alpha4=10$, applies the same principle to the number of comparators. These values for $\alpha1$, $\alpha2$, $\alpha3$, and $\alpha4$ were found to work well in this application, but the approach is not very sensitive to them. A broad range will work as long as they establish a primacy relationship between the objectives. Also, even though the composite multi-objective approach introduces these additional hyper parameters, they do not usually require significant tuning. Their values arise naturally from the problem domain based on how some solutions are preferred over others. For example, in the sorting network domain the values can easily be set to push system toward prioritizing number of layers over comparators if so desired.

In order to measure how novel the solutions are, it is first necessary to be able to characterize their behavior. While there are many ways to do it, a concise and computationally efficient way is to count how many swaps took place on each line in sorting all possible zero-one combinations during the validity check. Such a characterization is a vector that has the same size as the problem, making the distance calculations very fast. It also represents the true behavior of the network; that is, even if two networks sort the same input cases correctly, they may do it in different ways, and the characterization is likely to capture that difference. Given this behavior characterization, novelty of a solution is then measured by the sum of pairwise distances of its behavior vector to those of all the other individuals in the selection pool in accordance with equation (4) above.

The selection method also has another parameter called selection multiplier (e.g., two in this experiment), varying between one and the inverse of the elite fraction (e.g. 1/10, i.e. 10%) used in the NSGA-II multi-objective optimization method. The original selection percentage is multiplied by the selection multiplier to form a broader selection pool. That pool is sorted according to novelty, and the top fraction representing the original selection percentage is used for selection. This way, good solutions that are more novel are included in the pool. One potential issue is that a cluster of solutions far from the rest may end up having high novelty scores while only one of them is good enough to keep. Therefore, after the top fraction is selected, the rest of the sorted solutions are added to the selection pool one by one, replacing the solution with the lowest minimum novelty, defined as $$\text{Minimum}Novelty(x_i) = \min_{1 \leq j \leq n; j \neq i} d(b(x_i), b(x_j)). \qquad (10)$$

Note that this method allows tuning novelty selection continuously between two extremes: by setting it to one, the method reduces to the original multi-objective method (i.e., only the elite fraction ends up in the final elitist pool), and by setting it to the inverse of the elite fraction reduces it to pure novelty search (i.e., the whole population, sorted by novelty, is the selection pool). In practice, low and midrange values work well, including the value two used in these experiments.

Each of the methods was evaluated against the problem of discovering minimal sorting networks, and results were evaluated in terms of correctness and minimization.

In order to evaluate the composite novelty method in comparison to the identified pre-existing methods, 480 experiments were run with the following parameters:
  i. Four methods tested (Single Objective, Multi-Objective, Composite Multi-Objective, and Composite Multi-Objective Novelty; Multi-Objective Novelty was excluded because it showed no comparable improvements in preliminary experiments)
  ii. Twelve network sizes (5 through 16)
  iii. Ten repetitions for each configuration
  iv. Population of one thousand for the pool
  v. A thousand generations runtime
  vi. 10% elitist selection All 480 experiments were able to find solutions (individuals) that sort all inputs correctly. It is relatively easy to keep adding comparators until the network sorts everything correctly; there is little deception. The challenge comes from having to do it with minimal comparators and layers. Removing a comparator may require changing the network drastically to make it still sort correctly. Thus, although minimization is a secondary objective in constructing sorting networks, it is actually the more challenging one.

Minimization performance of the four methods is illustrated in FIGS. 10*a*-10*d*. The smallest known solution is also plotted for comparison (lower is better). The five-line sorting problem is simple enough so that all methods were able to discover optimal solutions in all runs. The methods' performance started to diverge from six lines on, and the differences became more pronounced the larger the problem.

Figure 10A:
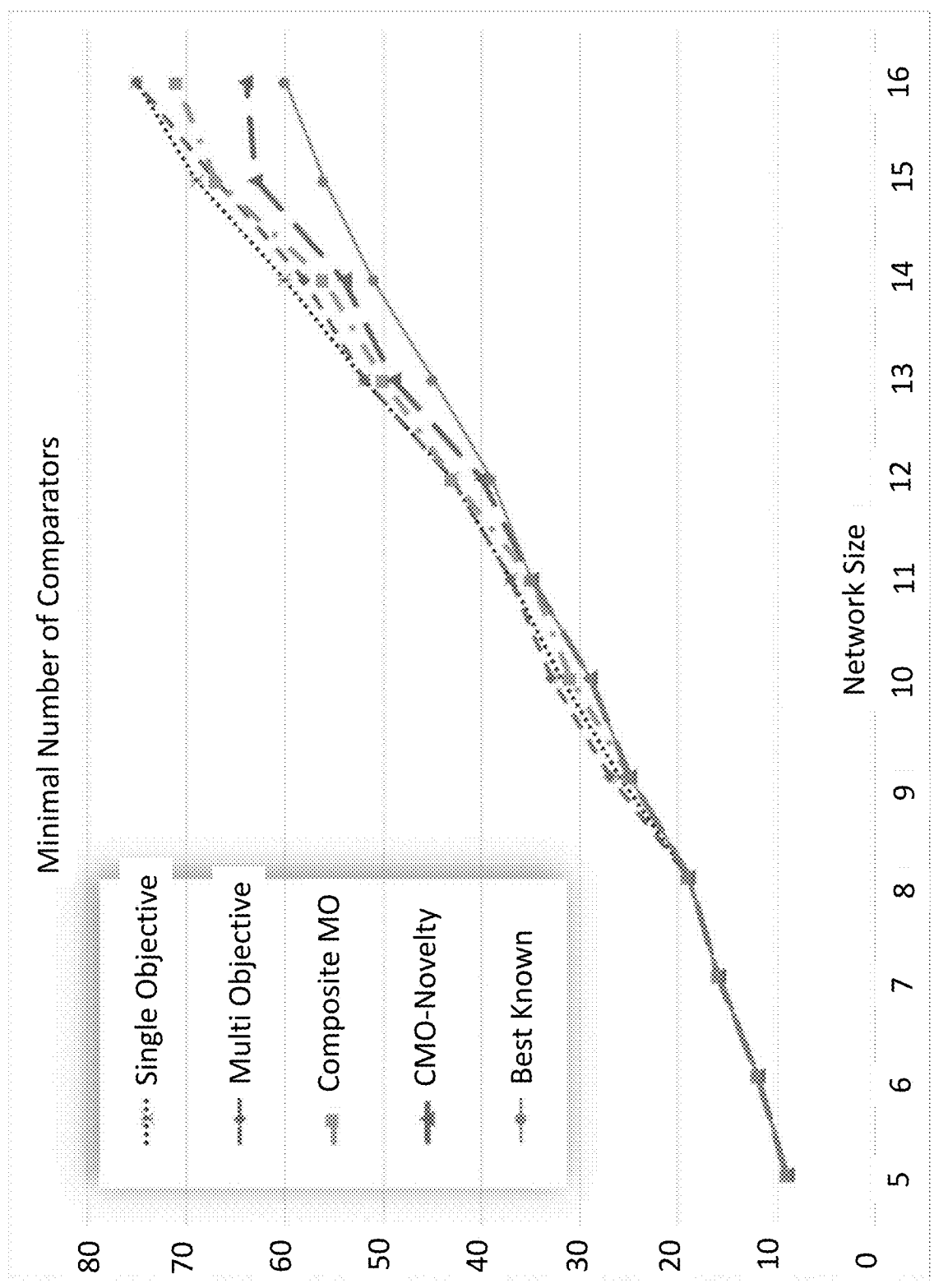
FIGS. 10a to 10d are graphs comparing minimization performance of the four methods used to address the problem of minimal sorting networks as discussed herein.
Figure 10B:
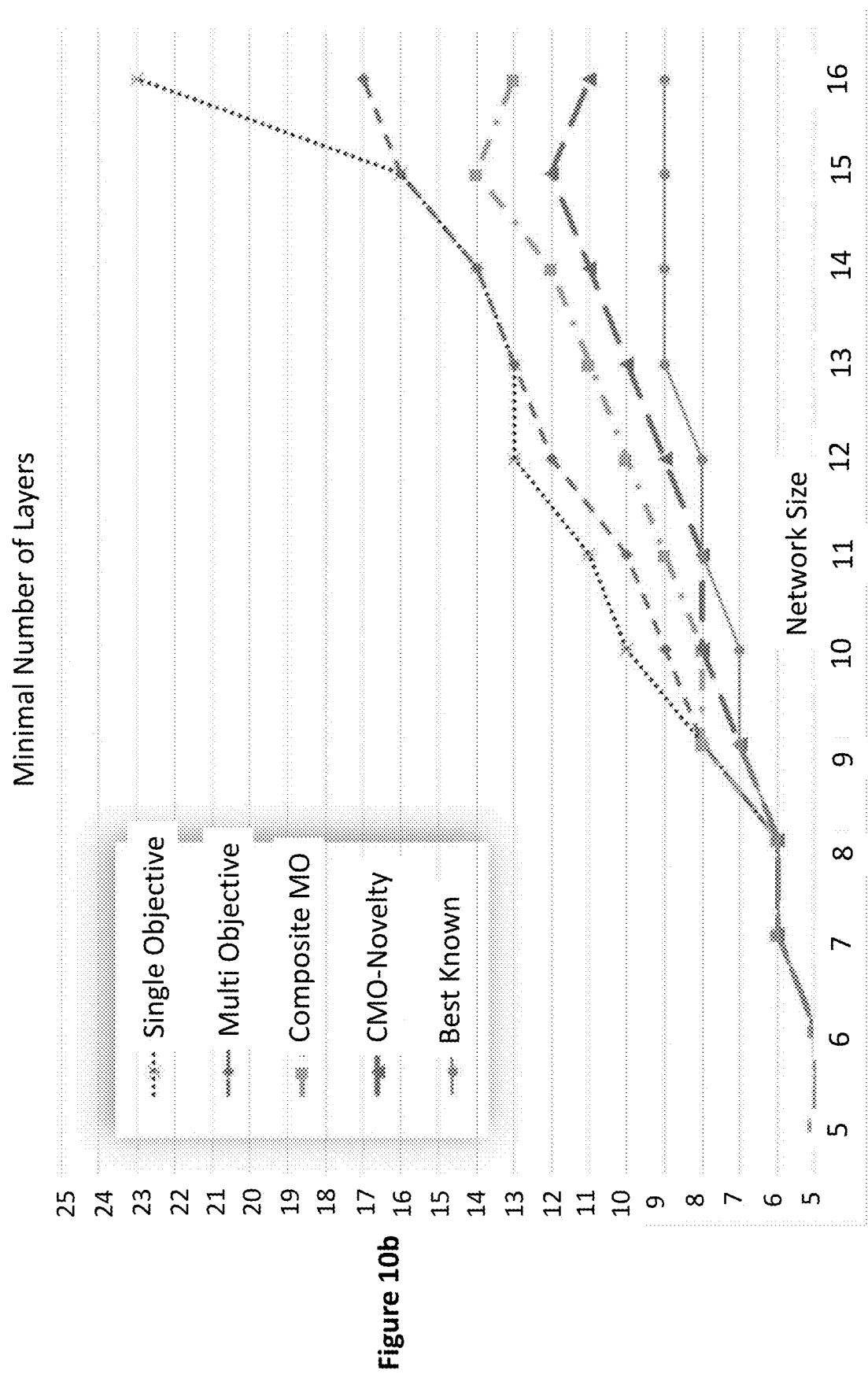
Figure 10C:
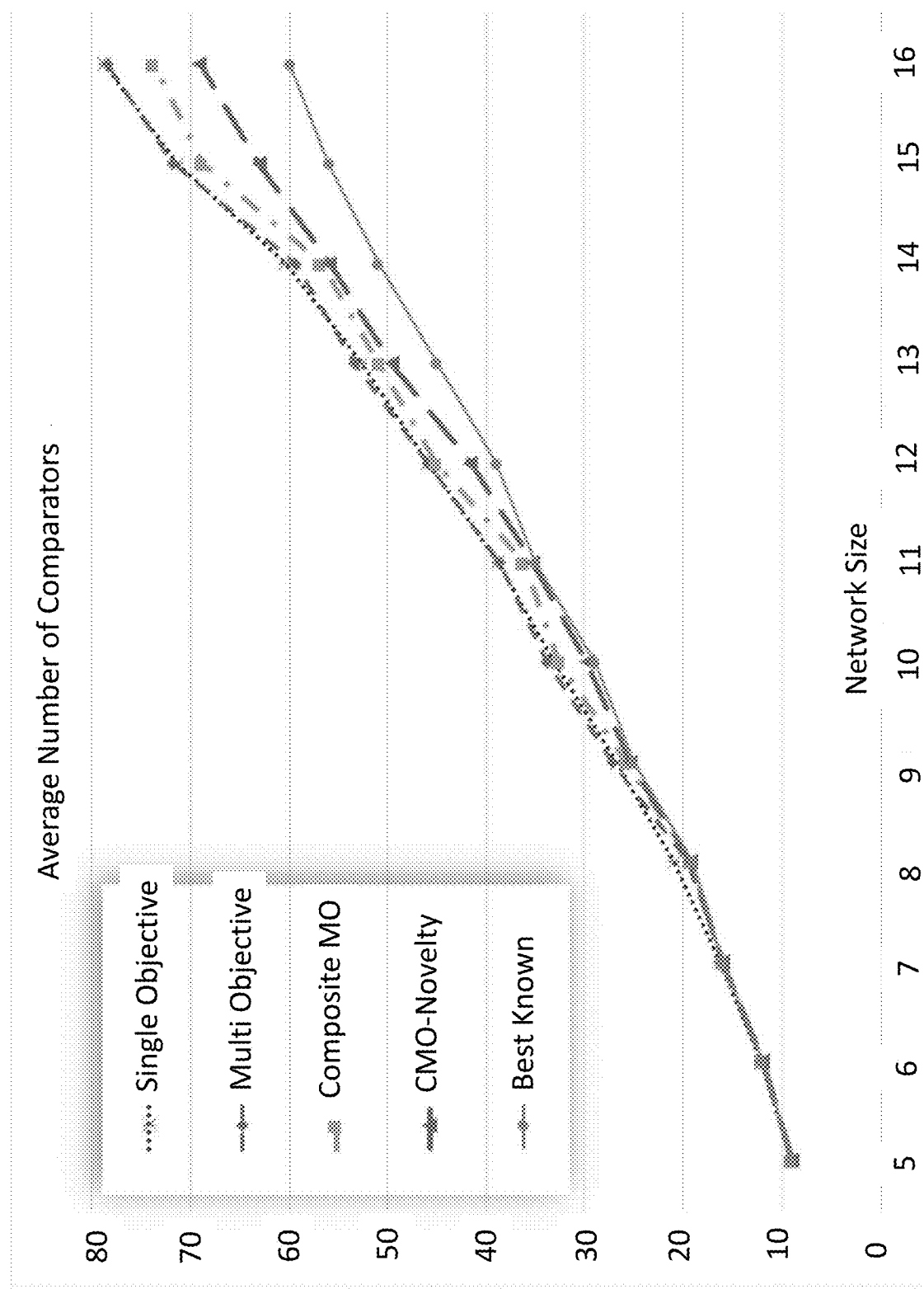
Figure 10D:
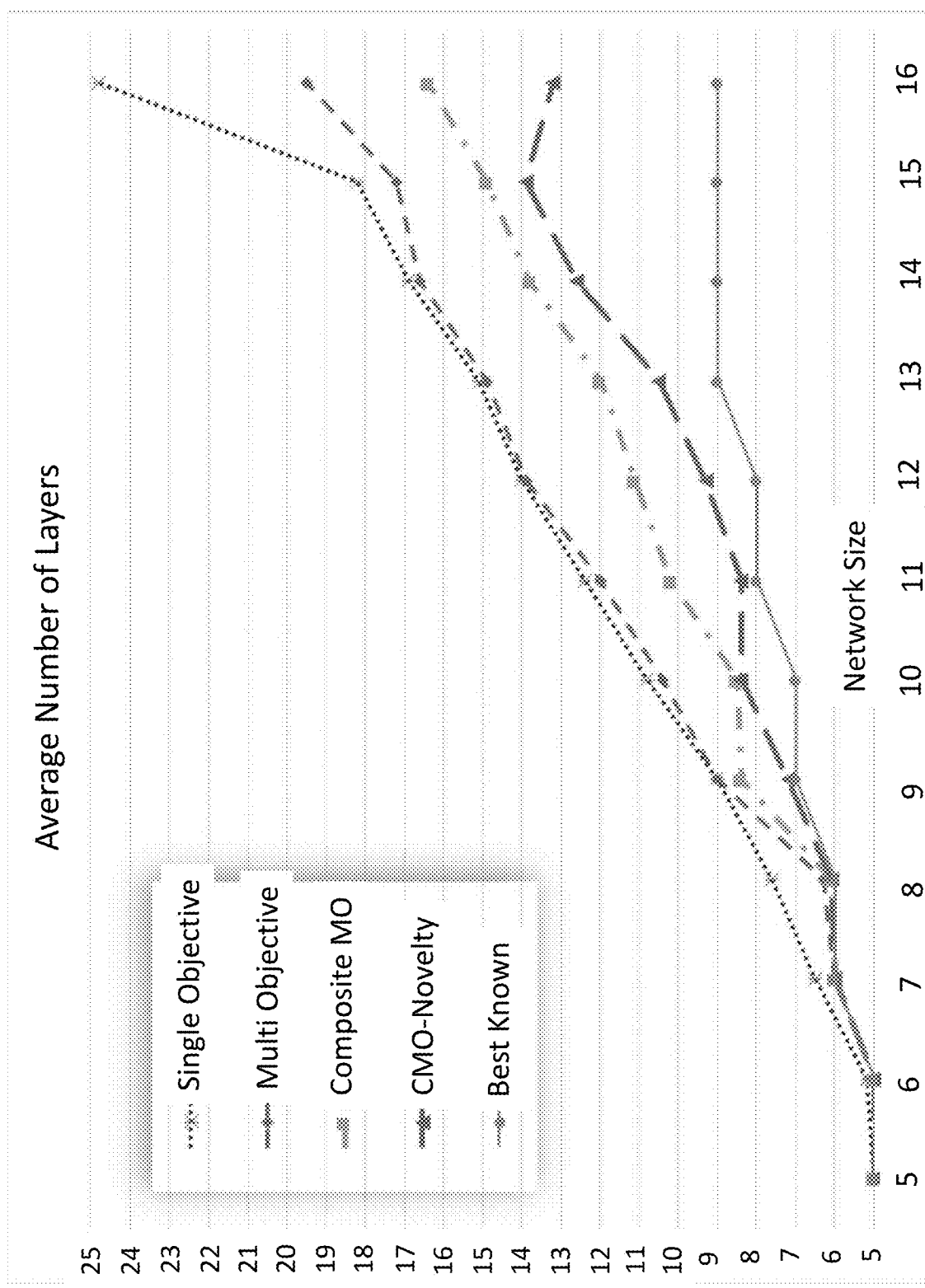

FIG. 10*a* shows the best runs in terms of comparators, and FIG. 10*b* in terms of number of layers. The Composite Multi-Objective Novelty method performs the best, followed by Composite Multi-Objective, Multi-Objective, and Single-Objective method. The average results follow a similar pattern. FIG. 10*c* shows the number of comparators and FIG. 10*d* the average number of layers in the best solutions found, averaged over the ten runs. Again, the Composite Multi-Objective Novelty method performs the best, followed by Composite Multi-Objective, Multi-Objective, and Single-Objective methods. In terms of statistical significance ($p<0.05$), the Multi-Objective approach achieves significant improvement over Single-Objective at 16-lines networks, while Composite Multi-Objective significantly outperforms Multi-Objective all the way from 9-lines to 16 lines. Composite Multi-Objective Novelty is better than Composite Multi-Objective in most networks after 11-lines.

The composite novelty method can also be applied in many other domains, in particular those that are deceptive and have natural secondary objectives. For instance, various game strategies from board to video games can be cast in this form, where winning is accompanied by different dimensions of the score. Solutions for many design problems, such as 3D printed objects, need to satisfy a set of functional requirements, but also maximize strength and minimize material. Effective control of robotic systems need to accomplish a goal while minimize energy and wear and tear. Thus, many applications should be amenable to this approach.

Another application is to extend the composite novelty method further into discovering effective collections of solutions. For instance, ensembling is a good approach for increasing the performance of machine learning systems. Usually the ensemble is formed from solutions with different initialization or training, with no mechanism to ensure that their differences are useful. In composite novelty, the Pareto front consists of a diverse set of solutions that span the area of useful tradeoffs. Such collections should make for a powerful ensemble, extending the applicability of the approach.

Alternate Embodiments

There are many embodiments evolving individuals in an evolutionary algorithm. The approach described herein may be implemented by any of the following embodiments.

In an embodiment, the evolutionary algorithm is distributed across multiple computers. The computers may be assigned a role of coordinator, mid-level coordinator, or evolutionary engine in which an evolutionary engine initializes, procreates, tests, and scores individuals, and coordinators compare individuals across the evolutionary engine. This is a federated approach. See, for example, the above-incorporated U.S. Pat. No. 9,466,023.

In an embodiment, the number of training data samples or an individual is tested against is tracked in an indication of experience level, and only those individuals with similar experience levels are permitted to compete with each other for a place in the candidate pool. See, for example, the above-incorporated U.S. Pat. No. 8,909,570. The individuals selected as parents for procreation are selected from among the best scoring of the most experienced individuals.

In an embodiment, parents involved in procreation are removed from the candidate pool, and in other embodiments, they remain in the candidate pool.

Many other variations will be apparent to the reader.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "indicate" is used herein to mean the same as "identify."

Also as used herein, a given event or value is "responsive" to a predecessor event or value if the predecessor event or value influenced the given event or value. If there is an intervening processing element, step or time period, the given event or value can still be "responsive" to the predecessor event or value. If the intervening processing element or step combines more than one event or value, the signal output of the processing element or step is considered "responsive" to each of the event or value inputs. If the given event or value is the same as the predecessor event or value, this is merely a degenerate case in which the given event or value is still considered to be "responsive" to the predecessor event or value. "Dependency" of a given event or value upon another event or value is defined similarly.

Applicants hereby disclose in isolation each individual feature described herein and each combination of two or more such features, to the extent that such features or combinations are capable of being carried out based on the present specification as a whole in light of the common general knowledge of a person skilled in the art, irrespective of whether such features or combinations of features solve any problems disclosed herein, and without limitation to the scope of the claims. Applicants indicate that aspects of the present invention may consist of any such feature or combination of features. In view of the foregoing description, it will be evident to a person skilled in the art that various modifications may be made within the scope of the invention.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. For example, dominance estimate for individuals in candidate individual pool 116 can in some embodiments be made available for external retrieval and/or analysis through the use of an API (not shown). Further, and without limitation, any and all variations described, suggested or incorporated by reference in the Background section or the Cross References section of this patent application are specifically incorporated by reference into the description herein of embodiments of the invention. In addition, any and all variations described, suggested or incorporated by reference herein with respect to any one embodiment are also to be considered taught with respect to all other embodiments. The embodiments described herein were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

The invention claimed is:

1. A computer-implemented method for finding a solution to a provided problem which optimizes a plurality of objectives, comprising the steps of:
   providing a computer system having a memory storing a candidate pool database identifying a pool of candidate individuals, each identifying a respective candidate solution to the provided problem;
   a computer system testing individuals from the pool of candidate individuals against a portion of training data to develop a plurality of objective values for each of the tested individuals, each of the objective values estimating the individual's level of success with respect to a corresponding one of the objectives;
   a computer system using a predefined dominance filter to select a first subset of individuals from the candidate pool database, the dominance filter being dependent upon a plurality of composite functions of the objectives, each of the composite functions being dependent on at least one of the of objectives and at least one of the composite functions being dependent on more than one of the objectives;
   a computer system selecting a second subset of individuals from the first subset of individuals, including selecting from the second subset of individuals a predetermined number of individuals having greater average behavioral novelty among the individuals in the first subset of individuals, than the average behavioral novelty of all others of the individuals from the first subset;
   a computer system procreating new individuals from a final subset of the individuals in the candidate pool database, the final subset being dependent upon the second subset of individuals;
   inserting the new individuals into the candidate pool database and repeating the steps of testing, selecting and procreating for multiple generations, wherein each iteration of the steps of testing, selecting and procreating is a generation;
   selecting at least one individual from the candidate pool database after a predetermined number of generations;
   a production system for applying the selected at least one individual to production data in real-time to generate a signal for automatically operating a controlled system; and
   operating a controlled system in dependence upon at least one of the individuals from the candidate pool database, wherein the controlled system is selected from the group consisting of a mechanical system, a computer system, and an output device, and further wherein the output device is selected from the group consisting of a visual output device and an audio output device.

2. The method of claim 1, further comprising a step, after each repetition of the step of selecting a second subset of individuals and prior to each subsequent repetition of the step of procreating new individuals from individuals in a final subset of the individuals, of:
   forming a third subset of individuals which is the subset of individuals from the first subset of individuals which are not selected into the second subset of individuals; and
   substituting individuals from the third subset of individuals into the second subset of individuals in a manner that improves the behavioral diversity of the individuals in the second set of individuals, to form the final set of individuals.

3. The method of claim 2, wherein substituting individuals from the third subset of individuals into the second subset of individuals comprises:
   adding an individual from the third subset of individuals to the second subset of individuals;
   selecting a pair of individuals from the second set of individuals that are least diverse from each other; and
   discarding one individual from the pair in dependence upon a predetermined filter until the number of individuals in the third set of individuals reaches zero.

4. The method of claim 3, wherein the predetermined filter is a dominance filter.

5. The method of claim 1, wherein using a predefined dominance filter to select a first subset of individuals from the candidate pool database comprises selecting from the first subset of individuals, individuals from the pool of candidate individuals that, in accordance with the predefined dominance filter, are not dominated by any other individuals in the pool.

6. The method of claim 5, wherein the predefined dominance filter is defined such that a first individual dominates over a second individual if and only if
   (a) a composite value of the first individual is better than a composite value of the second individual for at least one of the composite functions and
   (b) for all others of the composite functions, the composite value of the first individual is not worse than the composite value of the second individual.

7. The method of claim 1, where the average behavioral novelty for each individual $x_i$ is determined by the following:

$$\text{Average novelty score } (x_i) = \Sigma_{j=1}^{n} d(b(x_i), b(x_j))$$

wherein b(x) is a behavioral value of an individual x and a behavioral difference between $x_i$ and $x_j$ is a distance between two individuals in a behavior space.

8. A computer-implemented method for finding one or more optimal solutions to a predetermined problem wherein the one or more optimal solutions addresses a plurality of objectives, comprising:

testing by a first computer-implemented program each candidate solution from a predetermined pool of candidate solutions against a portion of training data to develop objective values for each of the tested candidate solution, each of the objective values estimating the candidate solution's level of success with respect to a corresponding one of the plurality of objectives;

selecting by a second computer-implemented program a first subset of candidate solutions from the candidate pool by application of a dominance filter, wherein the dominance filter compares a plurality of composite functions for each candidate solution in the first subset against other candidate solutions in the first subset, wherein the plurality of composite functions are dependent on the plurality of objectives and at least one of the composite functions being dependent on more than one of the objectives;

selecting by a third computer-implemented program a second subset of a predetermined number of candidate solutions from the first subset of candidate solutions, wherein each of the candidate solutions in the second subset has greater average behavioral novelty among the candidate solutions in the first subset of candidate solutions, than the average behavioral novelty of all others of the candidate solutions from the first subset;

selecting by a fourth computer-implemented program a final subset of candidate solutions from the second subset of candidate solutions, the final subset of candidate solutions containing the one or more optimal solutions to the predetermined problem;

applying at least one candidate solution from the final subset of candidate solutions to the predetermined problem in real-time to generate a signal for automatically operating a controlled system; and operating the controlled system in dependence upon at least one candidate solution, wherein the controlled system is selected from the group consisting of a mechanical system, a computer system, and an output device, and further wherein the output device is selected from the group consisting of a visual output device and an audio output device.

9. The method of claim 8, wherein application of the dominance filter to select a first subset of candidate solutions comprises selecting candidate solutions that are not dominated by any other candidate solutions in the candidate pool.

10. The method of claim 9, wherein the dominance filter is defined such that a first candidate solutions dominates over a second candidate solutions if and only if (a) a composite value of the first candidate solution is better than a composite value of the second candidate solutions for at least one of the composite functions and (b) for all others of the composite functions, the composite value of the first candidate solutions is not worse than the composite value of the second candidate solutions.

11. The method of claim 8, where the average behavioral novelty for each individual $x_i$ is determined by the following:

Average novelty score $(x_i) = \Sigma_{j=1}^{n} d(b(x_i), b(x_j))$ wherein b(x) is a behavioral value of an individual x and a behavioral difference between $x_i$ and $x_j$ is a distance between two individuals in a behavior space.

12. A computer-implemented method for finding one or more optimal solutions to a predetermined problem wherein the one or more optimal solutions addresses a plurality of objectives, comprising:

testing by a first computer-implemented program each candidate solution from a predetermined pool of candidate solutions against a portion of training data to develop objective values for each of the tested candidate solution, each of the objective values estimating the candidate solution's level of success with respect to a corresponding one of the plurality of objectives;

selecting by a second computer-implemented program a first subset of candidate solutions from the candidate pool by application of a dominance filter, wherein the dominance filter compares a plurality of composite functions for each candidate solution in the first subset against other candidate solutions in the first subset, wherein the plurality of composite functions are dependent on the plurality of objectives and at least one of the composite functions being dependent on more than one of the objectives;

selecting by a third computer-implemented program a second subset of a predetermined number of candidate solutions from the first subset of candidate solutions, wherein each of the candidate solutions in the second subset has greater average behavioral novelty among the candidate solutions in the first subset of candidate solutions, than the average behavioral novelty of all others of the candidate solutions from the first subset;

forming by a fourth computer-implemented program a third subset of candidate solutions which is a remaining subset of candidate solutions from the first subset of candidate solutions which are not selected into the second subset of candidate solutions; and substituting candidate solutions from the third subset of candidate solutions into the second subset of individuals in a manner that improves the behavioral diversity of the individuals in the second set of individuals, to form a final set of candidate solutions, the final subset of candidate solutions containing the one or more optimal solutions to the predetermined problem;

applying at least one optimal solution from the final subset of optimal solutions to the predetermined problem in real-time to generate a signal for automatically operating a controlled system; and operating the controlled system in dependence upon at least one candidate solution, wherein the controlled system is selected from the group consisting of a mechanical system, a computer system, and an output device, and further wherein the output device is selected from the group consisting of a visual output device and an audio output device.

13. The method of claim 12, wherein substituting candidate solutions from the third subset of candidate solutions into the second subset of candidate solutions comprises:

adding a candidate solution from the third subset of candidate solutions to the second subset of candidate solutions;

selecting a pair of candidate solutions from the second set of candidate solutions that are least diverse from each other; and discarding one candidate solutions from the pair in dependence upon a predetermined filter until the number of candidate solutions in the third set of candidate solutions reaches zero.

14. The method of claim 12, wherein application of the dominance filter to select a first subset of candidate solutions comprises selecting candidate solutions that are not dominated by any other candidate solutions in the candidate pool.

15. The method of claim 14, wherein the dominance filter is defined such that a first candidate solutions dominates over a second candidate solutions if and only if
   (a) a composite value of the first candidate solution is better than a composite value of the second candidate solutions for at least one of the composite functions and
   (b) for all others of the composite functions, the composite value of the first candidate solutions is not worse than the composite value of the second candidate solutions.

16. The method of claim 12, where the average behavioral novelty for each individual $x_i$ is determined by the following:

$$\text{Average novelty score } (x_i) = \Sigma_{j=1}^n d(b(x_i), b(x_j))$$

wherein $b(x)$ is a behavioral value of an individual x and a behavioral difference between $x_i$ and $x_j$ is a distance between two individuals in a behavior space.

* * * * *